United States Patent [19]

Spada et al.

[11] Patent Number: 5,364,862

[45] Date of Patent: Nov. 15, 1994

[54] COMPOUNDS HAVING ANTIHYPERTENSIVE AND ANTI-ISCHEMIC PROPERTIES

[75] Inventors: Alfred P. Spada, Lansdale; Cynthia A. Fink, Doylestown; Michael R. Myers, Reading, all of Pa.

[73] Assignee: Rhone-Poulenc Rorer Pharmaceuticals Inc., Collegeville, Pa.

[21] Appl. No.: 955,783

[22] Filed: Oct. 2, 1992

Related U.S. Application Data

[63] Continuation-in-part of Ser. No. 587,884, Sep. 25, 1990, abandoned.

[51] Int. Cl.$^5$ ...................... A61K 31/44; C07D 471/04
[52] U.S. Cl. ...................................... 514/303; 546/118
[58] Field of Search ........................... 546/118; 514/303

[56] References Cited

U.S. PATENT DOCUMENTS

| | | | |
|---|---|---|---|
| 3,502,649 | 3/1970 | Thiel et al. | 260/211.5 |
| 3,914,415 | 11/1975 | Stein et al. | 424/180 |
| 4,167,565 | 9/1979 | Stein et al. | 424/180 |
| 4,501,735 | 2/1985 | Trivedi et al. | 514/46 |
| 4,593,019 | 6/1986 | Bristol et al. | 514/46 |
| 4,600,707 | 7/1986 | Patt | 514/46 |
| 4,636,493 | 7/1987 | Patt | 514/46 |
| 4,657,897 | 4/1987 | Bristol et al. | 514/47 |
| 4,657,898 | 4/1987 | Bristol et al. | 514/46 |
| 4,663,313 | 5/1987 | Bristol et al. | 514/46 |
| 4,683,223 | 7/1987 | Trivedi et al. | 514/46 |
| 4,738,954 | 4/1988 | Hamilton et al. | 514/46 |
| 4,843,066 | 6/1989 | Yaamada et al. | 514/45 |
| 4,853,386 | 8/1989 | Friebe et al. | 514/266 |
| 4,954,504 | 9/1990 | Chen et al. | 514/265 |
| 4,968,697 | 11/1990 | Hutchison | 514/46 |
| 4,977,144 | 12/1990 | Fujimoto et al. | 514/46 |
| 5,032,583 | 7/1991 | Evans | 514/46 |
| 5,043,325 | 8/1991 | Olsson et al. | 514/46 |
| 5,063,233 | 11/1991 | Chen et al. | 514/266 |

FOREIGN PATENT DOCUMENTS

| | | |
|---|---|---|
| 181129 | 5/1986 | European Pat. Off. . |
| 232813 | 8/1987 | European Pat. Off. . |
| 277917 | 8/1988 | European Pat. Off. . |
| 354180 | 7/1989 | European Pat. Off. . |
| 378518 | 7/1990 | European Pat. Off. . |
| 409595 | 1/1991 | European Pat. Off. . |
| 2131938 | 1/1972 | Germany . |
| 2059922 | 6/1972 | Germany . |
| 2139107 | 2/1973 | Germany . |
| 2151013 | 4/1973 | Germany . |
| 2205002 | 8/1973 | Germany . |
| 2136624 | 2/1976 | Germany . |
| 59-21928 | 4/1984 | Japan . |
| 677630 | 3/1969 | South Africa . |
| 2199036 | 6/1988 | United Kingdom . |
| 2226027 | 6/1990 | United Kingdom . |
| 8504882 | 11/1985 | WIPO . |
| 8803147 | 5/1988 | WIPO . |
| 8803148 | 5/1988 | WIPO . |
| 8808303 | 11/1988 | WIPO . |
| 9205177 | 4/1992 | WIPO . |

OTHER PUBLICATIONS

Cristalli et al. J. Med. Chem. 31(6), 1179–83, 1988.
Baxter, et al., "Synthesis and Biological Activity of Carbocyclic Clitocine", Nucleosides and Nucleotides 10(1–3), 393–396 (1991).

(List continued on next page.)

*Primary Examiner*—Mukund J. Shah
*Assistant Examiner*—Y. N. Gupta
*Attorney, Agent, or Firm*—Paul R. Darkes; Martin F. Savitzky

[57] ABSTRACT

This invention relates to adenosine derivatives and analogs which possess adenosine agonist activity and are useful as anti-hypertensive and anti-ischemic agents, to pharmaceutical compositions including such compounds, and to their use in treating hypertension and myocardial ischemia, and to methods and intermediates used in the preparation of such compounds.

18 Claims, No Drawings

OTHER PUBLICATIONS

Prasad, et al., "Modification for the 5' Position of Purine Nucleosides. 2, Synthesis and Some Cardiovascular Properties of", J. Med. Chem. 1980, 23, pp. 313–319.

Houston, et al., "Potential Inhibitors of S–Adenosylmethionine–Dependent Methyltransferasess, 9, 2',3'-Diaaldehyde Derivatives", J. Med. Chem. 1985, 28, pp. 471–477.

Franchetti, et al., "Synthesis of 3-Deazaclitocine[-2-Amino-3-Nitro-4 (Beta-D Ribofuraanosylvaamino)-pyridine]", Nucleosides & Nucleotides, 10(1-3), 543-545-1991.

Prasad, et al., "Modification of the 5' Position of Purine Nucleosides. 1. Synthesis and Biological Properties of Alkyl", J. Med. Chem., 1976, vol. 19, No. 10, pp. 1180–1186.

Cristalli, et al., "Adenosine and 2-Chloradenosine Deaza#Analoges as Adenosine receptor aagonists", Nucleosides & Nucleotides, 4(5), 625–639 (1985).

Antonini, et al, "Deaza Analogues of Adenosine as Inhibitors of Blood Platelet Aggregation", Journal of Pharmaceutical Sciences, pp. 366–368 vol. 73, No. 3, Mar. 1984.

COMPOUNDS HAVING ANTIHYPERTENSIVE AND ANTI-ISCHEMIC PROPERTIES

This application is a continuation-in-part application of co-pending U.S. application Ser. No. 07/587,884, filed Sep. 25, 1990 now abandoned, and priority benefit is also claimed, pursuant to 37 U.S.C. §§ 120 and 363, to co-pending PCT Application PCT/US91/06990, filed Sep. 25, 1991.

BACKGROUND OF THE INVENTION

1. Field of the Invention

This invention relates to compounds derived from adenosine and analogs thereof, to pharmaceutical compositions containing such compounds, to their use in treating hypertension and myocardial ischemia, and to methods and intermediates used in the preparation of such compounds.

Hypertension

Hypertension, a condition of elevated blood pressure, affects a substantial number of the human population. Consequences of persistent hypertension include vascular damage to the ocular, renal, cardiac and cerebral systems, and the risk of these complications increases as blood pressure increases. Basic factors controlling blood pressure are cardiac output and peripheral vascular resistance, with the latter being the predominant common mechanism which is controlled by various influences. The sympathetic nervous system regulates peripheral vascular resistance through direct effects on alpha- and beta-adrenergic receptors as well as through indirect effects on renin release. Drug therapy is aimed at specific components of these blood pressure regulatory systems, with different mechanisms of action defining the several drug classes including diuretics, beta-adrenergic receptor antagonists (beta-blockers), angiotensin-converting enzyme (ACE) inhibitors, and calcium channel antagonists.

Thiazide-type diuretics are used in hypertension to reduce peripheral vascular resistance through their effects on sodium and water excretion. This class of drugs includes hydrochlorothiazide, chlorothiazide, methyclothiazide, and cyclothiazide, as well as related agents indapamide, metolazone, and chlorthalidone. Although the beta-blocker mechanism of action was once believed to be blockade of the beta$_1$-adrenergic receptor subtype in the heart to reduce heart rate and cardiac output, more recent beta-blockers with intrinsic sympathomimetic activity (ISA), including pindolol, acebutolol, penbutolol, and carteolol, are as effective as non-ISA beta-blockers, causing less reduction in heart rate and cardiac output. Other postulated mechanisms for these drugs include inhibition of renin release, a central effect, and an effect at pre-synaptic beta-adrenergic receptors resulting in inhibition of norepinephrine release. Cardioselective beta-blockers metoprolol (Lopressor-Geigy), acebutolol (Sectral-Wyeth), and atenolol (Tenormin-ICI), at low doses, have a greater effect on beta$_1$-adrenergic receptors than on beta$_2$-adrenergic receptor subtypes located in the bronchi and blood vessels. Nonselective beta-blockers act on both beta-adrenergic receptor subtypes and include propranolol (Inderal-Ayerst), timolol (Blocadren-Merck), nadolol (Corgard-Squibb), pindolol (Visken-Sandoz), penbutolol (Levatol-Hoechst-Roussel), and carteolol (Cartrol-Abbott). Adverse effects of beta-blockers include asymptomatic bradycardia, exacerbation of congestive heart failure, gastrointestinal disturbances, increased airway resistance, masked symptoms of hypoglycemia, and depression. They may cause elevation of serum triglycerides and may lower high-density lipoprotein cholesterol.

ACE inhibitors prevent the formation of angiotensin II and inhibit breakdown of bradykinin. Angiotensin II is a potent vasoconstrictor and also stimulates the secretion of aldosterone. By producing blockade of the renin-angiotensin-aldosterone system, these agents decrease peripheral vascular resistance, as well as sodium and water retention. In addition, ACE inhibitors increase levels of bradykinin and prostaglandins, endogenous vasodilators. Captopril (Capoten-Squibb) and Enalapril (Vasotec-Merck) are the leading ACE inhibitors. Adverse effects of the ACE inhibitors include rash, taste disturbance, proteinuria, and neutropenia.

The calcium channel antagonists reduce the influx of calcium into vascular smooth muscle cells and produce systemic vasodilation, resulting in their antihypertensive effect. Other effects of calcium channel antagonists include interference with action of angiotensin II and alpha$_2$-adrenergic receptor blockade, which may add to their antihypertensive effects. Calcium channel antagonists do not have the adverse metabolic and pharmacologic effects of thiazides or beta-blockers and may therefore be useful in patients with diabetes, peripheral vascular disease, or chronic obstructive pulmonary disease. Two calcium channel antagonists, Verapamil and diltiazem, have serious adverse cardiovascular effects on atrioventricular cardiac conduction in patients with preexisting conduction abnormalities, and they may worsen bradycardia, heart block, and congestive heart failure. Other minor adverse effects of calcium channel antagonists include peripheral edema, dizziness, light-headedness, headache, nausea, and flushing, especially with nifedipine and nicardipine.

Many other agents are available to treat essential hypertension. These agents include prazosin and terazocin, alpha$_1$-adrenergic receptor antagonists whose antihypertensive effects are due to resultant arterial vasodilation; clonidine, an alpha$_2$-adrenergic agonist which acts centrally as well as peripherally at inhibitory alpha$_2$-adrenergic receptors, decreasing sympathetic response. Other centrally acting agents include methyldopa, guanabenz, and guanfacine; reserpine, which acts by depleting stores of catecholamines; guanadrel, a peripheral adrenergic antagonist similar to guanethidine with a shorter duration of action; and direct-acting vasodilators such as hydralazine and minoxidil. These agents, although effective, produce noticeable symptomatic side effects, including reflex sympathetic stimulation and fluid retention, orthostatic hypotension, and impotence.

Many antihypertensive agents activate compensatory pressor mechanisms, such as increased renin release, elevated aldosterone secretion and increased sympathetic vasoconstrictor tone, which are designed to return arterial pressure to pretreatment levels, and which can lead to salt and water retention, edema and ultimately to tolerance to the antihypertensive actions of the agent. Furthermore, due to the wide variety of side effects experienced with the present complement of antihypertensive drugs and the problems experienced therewith by special populations of hypertensive patients, including the elderly, blacks, and patients with chronic obstructive pulmonary disease, diabetes, or peripheral vascular diseases, there is a need for additional classes of drugs to treat hypertension.

Ischemia

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone. Mechanisms for vasospastic ischemia include: (i) Increased vascular tone at the site of stenosis due to increased catecholamine release: (ii) Transient intraluminal plugging and (iii) Release of vasoactive substances formed by platelets at the site of endothelial lesions.

The coronary circulation is unique since it perfuses the organ which generates the perfusion pressure for the entire circulation. Thus, interventions which alter the state of the peripheral circulation and contractility will have a profound effect on coronary circulation. The regulatory component of the coronary vasculature is the small coronary arterioles which can greatly alter their internal diameter. The alteration of the internal radius is the result of either intrinsic contraction of vascular smooth muscle (autoregulation) or extravascular compression due to ventricular contraction. The net effect of therapies on the ischemic problem involves a complex interaction of opposing factors which determine the oxygen supply and demand.

The present invention relates to the class of adenosine agonists and their utility in the treatment of hypertension and myocardial ischemia.

2. Reported Developments

Adenosine has a wide variety of physiological and pharmacological action including a marked alteration of cardiovascular and renal function. In animals and man, intravenous injection of the adenosine nucleotide causes hypotension.

The physiological and pharmacological actions of adenosine are mediated through specific receptors located on cell surfaces. Two adenosine receptor subtypes, designated as $A_1$ and $A_2$ receptors, have been identified. The $A_1$ receptor inhibits the formation of cAMP by suppressing the activity of adenylate cyclase, while stimulation of $A_2$ receptors increases adenylate cyclase activity and intracellular cAMP. Each receptor appears to mediate specific actions of adenosine in different tissues: for example, the vascular actions of adenosine appears to be mediated through stimulation of $A_2$ receptors, which is supported by the positive correlation between cAMP generation and vasorelaxation in adenosine-treated isolated vascular smooth muscle; while stimulation of the cardiac $A_1$ receptors reduces cAMP generation in the heart which contributes to negative dromotropic, inotropic and chronotropic cardiac effects. Consequently, unlike most vasodilators, adenosine administration does not produce a reflex tachycardia.

Adenosine also exerts a marked influence on renal function. Intrarenal infusion of adenosine causes a transient fall in renal blood flow and an increase in renal vascular resistance. With continued infusion of adenosine, renal blood flow returns to control levels and renal vascular resistance is reduced. The initial renal vasoconstrictor responses to adenosine are not due to direct vasoconstrictor actions of the nucleotide, but involve an interaction between adenosine and the renin-angiotensin system.

Adenosine is widely regarded as the primary physiological mediator of reactive hyperemia and autoregulation of the coronary bed in response to myocardial ischemia. It has been reported that the coronary endothelium possesses adenosine $A_2$ receptors linked to adenylate cyclase, which are activated in parallel with increases in coronary flow and that cardiomyocyte receptors are predominantly of the adenosine $A_1$ subtype and associated with bradycardia. Accordingly, adenosine offers a unique mechanism of ischemic therapy.

Cardiovascular responses to adenosine are short-lived due to the rapid uptake and metabolism of the endogenous nucleotide. In contrast, the adenosine analogs are more resistant to metabolic degradation and are reported to elicit sustained alterations in arterial pressure and heart rate.

Several potent metabolically-stable analogs of adenosine have been synthesized which demonstrate varying degrees of selectivity for the two receptor subtypes. Adenosine agonists have generally shown greater selectivity for $A_1$ receptors as compared to $A_2$ receptors. Cyclopentyladenosine (CPA) and R-phenylisopropyladenosine (R-PIA) are standard adenosine agonists which show marked selectivity for the $A_1$ receptor ($A_2/A_1$ ratio=780 and 106, respectively). In contrast, N-5'-ethyl-carboxamido adenosine (NECA) is a potent $A_2$ receptor agonist (Ki-12 nM) but has equal affinity for the $A_1$ receptor (Ki-6.3 nM; $A_2/A_1$ ration=1.87). Until recently, CV-1808 was the most selective $A_2$ agonist available ($A_2/A_1$=0.19), even though the compound was 10-fold less potent than NECA in its affinity for the $A_2$ receptor. In recent developments, newer compounds have been disclosed which are very potent and selective $A_2$ agonists (Ki=3–8 nM for $A_2/A_1$ ratio=0.0-27–0.042).

Various N6-aryl and N6-heteroarylalkyl substituted adenosines, and substituted-(2-amino and 2-hydroxy)adenosines, have been reported in the literature as possessing varied pharmacological activity, including cardiac and circulatory activity. See, for example, British Patent Specification 1,123,245, German Offen. 2,136,624, German Off 2,059,922, German Offen. 2,514,284, South African Patent No. 67/7630, U.S. Pat. No. 4,501,735, EP Publication No. 0139358 (disclosing N6-[geminal diaryl substituted alkyl]adenosines), EP Patent Application Ser. No. 88106818.3 (disclosing that N6-heterocyclic-substituted adenosine derivatives exhibit cardiac vasodilatory activity), German Often. 2,131,938 (disclosing aryl and heteroaryl alkyl hydrazinyl adenosine derivatives), German Often. 2,151,013 (disclosing N6-aryl and heteroaryl substituted adenosines), German Often. 2,205,002 (disclosing adenosines with N6-substituents comprising bridged ring structures linking the N6-nitrogen to substituents including thienyl) and South African Patent No. 68/5477 (disclosing N6-indolyl substituted-2-hydroxy adenosines).

U.S. Pat. No. 4,954,504 and EP Publication No. 0267878 disclose generically that carbocyclic ribose analogues of adenosine, and pharmaceutically acceptable esters thereof, substituted in the 2- and/or N6-positions by aryl lower alkyl groups including thienyl, tetrahydropyranyl, tetrahydrothiopyranyl, and bicyclic benzo fused 5- or 6- membered saturated heterocyclic lower alkyl derivatives exhibit adenosine receptor agonist properties. Adenosine analogues having thienyl-type substituents are described in EP Publication No. 0277917 (disclosing N6-substituted-2-heteroarylalkylamino substituted adenosines including 2-[(2-[thien-2-yl]ethyl)amino] substituted adenosine), German Often. 2,139,107 (disclosing N6-[benzothienylmethyl]-adenosine), PCT WO 85/04882 (disclosing that N6-heterocyclicalkyl-substituted adenosine derivatives, including N6-[2-(2thienyl)ethyl]amino-9-(D-ribofuranosyl)-9H-purine, exhibit cardiovascular vasodilatory activity and that N6-chiral substituents exhibit enhanced activity), EP Published Application No. 0232813 (disclosing that N6-(1-substituted thienyl)cyclopropylmethyl substituted adenosines exhibit cardiovascular activity), U.S. Pat. No. 4,683,223 (disclosing that N6-benzothiopyranyl substituted adenosines exhibit antihypertensive properties), PCT WO 88/03147 and WO 88/03148 (disclosing that N6-[2-aryl-2-(thien-2-yl)]ethyl substituted adensosines exhibit antihypertensive properties), U.S. Pat. Nos. 4,636,493 and 4,600,707 (disclosing that N6-benzothienylethyl substituted adenosines exhibit antihypertensive properties).

Adenosine-5'-carboxylic acid amides are disclosed as having utility as anti-hypertensive and anti-anginal agents in U.S. Pat. No. 3,914,415, while U.S. Pat. No. 4,738,954 discloses that N6-substituted aryl and arylalkyl-adenosine 5'-ethyl carboxamides exhibit various cardiac and antihypertensive properties.

$N^6$-alkyl-2'-O-alkyl adenosines are disclosed in EP Publication No. 0,378,518 and UK Patent Application 2,226,027 as having antihypertensive activity. $N^6$-alkyl-2',3'-di-O-alkyl adenosines are also reported to have utility as antihypertensive agents, U.S. Pat. No. 4,843,066.

Adenosine-5'-(N-substituted)carboxamides and carboxylate esters and N1-oxides thereof are reported to be coronary vasodilators, Stein, et al., *J. Med. Chem.* 1980, 23, 313–319 and *J. Med. Chem.* 19 (10), 1180 (1976). Adenosine-5'-carboxamides and N1-oxides thereof are also reported as small animal poisons in U.S. Pat. No. 4,167,565.

It is believed that the reported toxicity, CNS properties and heart rate elevation associated with adenosine analogues have contributed to the difficulties preventing the development of a commercial adenosine analog antihypertensive/antiischemic agent. The present invention relates to a class of metabolically stable adenosine agonists, and derivatives thereof, possessing unexpectedly desireable pharmacological properties, i.e. are anti-hypertensive and anti-ischemic agents having a unique therapeutic profile.

Summary of the Invention

The compounds of the present invention are described by Formula I

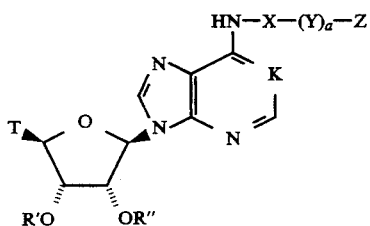

Formula I wherein

K is N, N→O, or CH;
Q is CH$_2$ or O;
T is R$_2$

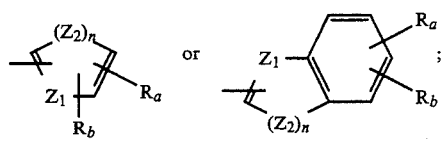

or R$_3$O—CH$_2$;

X is a straight or branched chain alkylene, cycloalkylene or cycloalkenylene group;
Y is NR$_4$, O or S;
a=0 or 1;
Z is of the formula

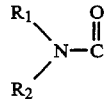

$Z_1$ is N, CR$_5$, (CH)$_m$—CR$_5$ or (CH)$_m$—N, m being 1 or 2;
$Z_2$ is N, NR$_6$, O or S, n being 0 or 1;
$R_1$, $R_2$, $R_3$, $R_4$, $R_5$ and $R_6$ are independently H, alkyl, aryl or heterocyclyl;
$R_a$ and $R_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl; and
R' and R" are independently hydrogen, alkyl, aralkyl, carbamoyl, alkyl carbamoyl, dialkylcarbamoyl, acyl, alkoxycarbonyl, aralkoxycarbonyl, aryloxycarbonyl, or R' and R" together may form

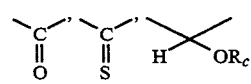

where R$_c$ is hydrogen or alkyl,

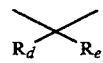

where R$_d$ and R$_e$ are independently hydrogen, alkyl, or together with the carbon atom to which they are attached may form a 1,1-cycloalkyl group;
provided that when X is straight chain alkylene and Q is oxygen, then Z represents a heterocyclyl including at least two heteroatoms;
or a pharmaceutically acceptable salt thereof.

This invention relates also to methods for treating cardiovascular disease marked by hypertension or myocardial ischemia using pharmaceutical compositions including an anti-hypertensive effective amount or an anti-ischemic effective amount of a compound of Formula I above, and to methods and intermediates used in the preparation of such compounds.

DETAILED DESCRIPTION

As used above and throughout the description of the invention, the following terms, unless otherwise indicated, shall be understood to have the following meanings:

"Acyl" means a straight or branched alkyl-C=0 group. Preferred acyl groups are lower alkanoyl having from 1 to about 6 carbon atoms in the alkyl group.

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain.

"Lower alkyl" means an alkyl group having 1 to about 6 carbons.

"Alkylene" means a straight or branched bivalent hydrocarbon chain having from 1 to about 20 carbon atoms. The preferred alkylene groups are the lower alkylene groups having from 1 to about 6 carbon atoms. The most preferred alkylene groups are methylene, ethylene, ethylethylene, methylethylene and dimethylethylene.

"Cycloalkylene" means a 1,2- or 1,3-bivalent carbocyclic group having about 4 to about 8 carbon atoms. Preferred cycloalkylene groups include 4, 5-cis- or trans-cyclohexenylene, 1,2-cyclohexanylene and 1,2-cyclopentylene.

"Alkyl amino" means an amino group substituted by one or two alkyl groups. Preferred groups are the lower alkyl amino groups.

"Alkyl carbamoyl" means a carbamoyl group substituted by one or two alkyl groups. Preferred are the lower alkyl carbamoyl groups.

"Alkyl mercaptyl" means an alkyl group substituted by a mercaptyl group. Mercaptyl lower alkyl groups are preferred.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group, as previously described, substituted by an alkoxy group, as previously described.

"Aralkyl" means an alkyl group substituted by an aryl radical, wherein "aryl" means a phenyl or phenyl substituted with one or more substituents which may be alkyl, alkoxy, amino, nitro, carboxy, carboalkoxy, cyano, alkyl amino, halo, hydroxy, hydroxyalkyl, mercaptyl, alkylmercaptyl, carbalkyl or carbamoyl.

"Carbalkoxy" means a carboxyl substituent esterified with an alcohol of the formula $C_nH_{2n+1}OH$, wherein n is from 1 to about 6.

"Halogen" (or "halo") means chlorine (chloro), fluorine (fluoro), bromine (bromo) or iodine (iodo).

"Heterocyclyl" means about a 4 to about a 10 membered ring structure in which one or more of the atoms in the ring is an element other than carbon, e.g., N, O, or S.

Representative heterocyclic moieties comprising the N6 substituent of the compounds of Formula I include the following:

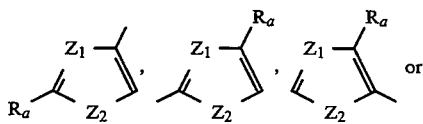

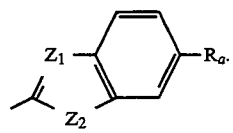

Preferred heterocyclic groups include unsubstituted and substituted thienyl, thiazolyl and benzothiazolyl groups, wherein the substituents may be one or more members of the group of alkoxy, alkylamino, aryl, carbalkoxy, carbamoyl, cyano, halo, hydroxy, mercaptyl, alkylmercaptyl or nitro.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl and 3-hydroxypropyl.

"Pro-drug" means a compound which may or may not itself be biologically active but which may, by metabolic, solvolytic, or other physiological means be converted to a biologically active chemical entity.

The compounds of Formula I include preferably a chiral (asymmetric) center. For example, preferred compounds having such asymmetric center comprise compounds e.g., wherein X is isopropylene, and have either an R or S configuration, the R configuration being most preferred. The invention includes the individual stereoisomers and mixtures thereof. The individual isomers are prepared or isolated by methods well known in the art or by methods described herein.

The compounds of the invention may be used in the form of the free base, in the form of acid addition salts or as hydrates. All such forms are within the scope of the invention. Acid addition salts are simply a more convenient form for use. In practice, use of the salt form inherently amounts to use of the base form. The acids which may be used to prepare the acid addition salts include preferably those which produce, when combined with the free base, pharmaceutically acceptable salts, that is, salts whose anions are non-toxic to the recipient in pharmaceutical doses of the salts, so that the beneficial anti-hypertensive and anti-ischemic effects produced by the free base are not vitiated by side effects ascribable to the anions. Although pharmaceutically acceptable salts of the compounds of the invention are preferred, all acid addition salts are useful as sources of the free base form, even if the particular salt, per se, is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid, and sulfamic acid; and organic acids such as acetic acid, citric acid, lactic acid, tartaric acid, malonic acid, methanesulfonic acid, fumaric acid, ethanesulfonic acid, benzenesulfonic acid, p-toluenesulfonic acid, cyclohexylsulfamic acid, quinic acid and the like. The corresponding acid addition salts comprise the following: hydrochloride, sulfate, phosphate, sulfamate, acetate, citrate, lactate, tartarate, methanesulfonate, fumarate, ethanesulfonate, benzenesulfonate, p-toluenesulfonate, cyclohexylsulfonate and quinate, respectively.

The acid addition salts of the compounds of the invention are conveniently prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Included within the scope of Formula I are classes of compounds which may be characterized generally as N6-heterocyclic-substituted adenosines; N6-heterocyclic-substituted carbocyclic adenosines (or, alternatively, dihydroxy[N6-heterocyclic substituted-9-adenyl]cyclopentanes) and N-oxides thereof; and N6-heterocyclic-substituted-N'-1-deazaaristeromycins (or, alternatively, dihydroxy[N7-heterocyclic-substituted[4,5-b]imidazopyridyl]-cyclopentanes). Also within the scope of Formula I are the 5'-alkylcarboxamide derivatives of the adenosines, the carbocyclic adenosines and the 1-deazaaristeromycins, the derivatives of compounds of the above classes in which one or both of the 2- or 3- hydroxyl groups of the cyclopentane ring or, in the cases of classes of compounds containing the ribose moiety, the 2'- or 3'-hydroxyl groups of the ribose ring are substituted. Such derivatives may themselves comprise the biologically active chemical entity useful in the treatment of hypertension and myocardial ischemia, or may act as pro-drugs to such biologically active compounds which are formed therefrom under physiological conditions.

Representative compounds of the invention include: N6-[trans-2-(thiophen-2-yl)cyclohex-4-en-1-yl]adenosine; N6-[trans-2-(thiophen-3-yl)-cyclohex-4-en-1 -yl]adenosine; N6-[trans-2-(thiophen-2-yl)cyclohex-4-en-1 -yl]adenosine-5'-N-ethyl carboxamide; N6-[2-(2'-aminobenzothiazolyl)ethyl]adenosine; N6-[2-(2'-thiobenzothiazolyl)ethyl]adenosine; N6-[2-(6'-ethoxy2'-thiobenzothiazolyl)ethyl]adenosine; N6-[2-(2'-aminobenzothiazolyl)ethyl]adenosine-5'-N-ethyl carboxamide; N6-[2-(2'-aminothiazolyl)ethyl]carbocyclic adenosine-5'-N-ethyl carboxamide; N6-[2-(4'-methyl-thiazol-5'-yl)ethyl]adenosine; N6-[2-(2'-thiazolyl)ethyl]adenosine; N6-[(R)-1-(5'-chlorothien-2'-yl)2-propyl]adenosine-5'-N-ethyl carboxamide; N6-[2-(2'-methyl-4'-thiazolyl)ethyl]adenosine; N6-[(R)-1 -methyl-2-(2'-benzo[b]thiophenyl)ethyl]adenosine; N6-[2-(4''-methyl-5''-thiazolyl)ethyl]carbocyclic adenosine-5'-N-ethyl carboxamide; N6-[2-(2''-thiazolyl)ethyl]carbocyclic adenosine-5'-N-ethyl carboxamide; N6-[2-( 4'-phenyl-2'-thiazolyl)ethyl]adenosine; N6-[(R)-1-(5''-chloro-2''-thienyl)prop-2-yl]carbocyclic adenosine-5'-N-ethyl carboxamide; (−)-N6-[thiophen-2''-yl)ethan-2-yl]carbocyclic adenosine-5'-N-ethyl carboxamide; N6-[1-(thiophen-3-yl)ethan-2-yl]carbocyclic adenosine-5'-N-ethyl carboxamide; N6-[(R)-1-((thiophen-2-yl)prop-2-yl)]carbocyclic adenosine-5'-N-ethyl carboxamide; N6-[1-(thiophen-2-yl)ethan-2-yl]-N'-1-deazaaristeromycin-5'-N-ethyl carboxamide; N6-[(R)-1-((thiazo-2-yl)-prop-2-yl)]adenosine-5'-N-ethyl carboxamide; N6-[1-(thiophen-2-yl)-2-methylpropyl]adenosine-5'-N-ethyl carboxamide; N6-[(R)-1-(5'-chlorothien-2yl)-2-butyl]carbocyclic adenosine-5'-N-ethylcarboxamide; N6-[2-(4'-methyl-2'-thiazolyl)ethyl]adenosine; N6-[4'-phenyl-2'-thiazolyl)-methyl]adenosine; (−)]2S-[2α,3α-dimethylmethylenedioxy-4-β-[N6-(5-chloro-2-thienyl)-(1R)-1-methylethyl-]amino]-9-adenyl]cyclopentane]-1-β-N-ethylcarboxamide; (2S)-2α,3α-dihydroxy-4β-[N6-[2-(5-chloro-2-thienyl)-(1R)-1-methylethyl]amino-9-adenyl]cyclopentane-1β-N-ethylcarboxamide; (2S)-2α,3α-dihydroxy-4β-[N6-[2-(5-chloro-2-thienyl)-(1R)-1-methylethyl]amino-9-adenyl]cyclopentane-1β-N-ethylcarboxamide-N¹-oxide; [1S-[1α, 2β,3β, 4α(S*)]]-4-[7-[[2-(5-chloro-2-thienyl)-1-methylethyl]amino]-3H-imidazo[4,5-b]pyridin-3-yl]-N-ethyl-2,3-dihydroxycyclopentanecarboxamide; [1S-[1α,2β,3β,4α]]-4-[7-[[2-(3-chloro-2-thienyl)-1-ethylethyl]amino]-3H-imidazo[4,5-b]pyridin-3-yl]-N-ethyl-2,3-dihydroxycyclopentanecarboxamide; [1S-[1α,2β,3β,4α]]-4-[7-[[2-(2-thienyl)-1-isopropylethyl]amino]-3H-imidazo[4,5-b]pyridin-3-yl]-N-ethyl-2,3-dihydroxycyclopentanecarboxamide; [1S-[1α,2β,3β,4α(S*)]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide; [1S-[1α,2β,3β,4α(S*)]]-4-[7-[[2-(2-thienyl)-1-methylethyl]amino]-3H-imidazo[4,5-b]pyridin-3-yl]-N- ethyl-2,3-dihydroxycyclopentane-carboxamide; [1S-[1α,2β,3β,-4α]]-4-[7-[[2-(5-chloro-2-thienyl)-1-ethylethyl]amino]-3H-imidazo[4,5-b]pyridin-3-yl]-N-ethyl-2,3-dihydroxycyclopentane-carboxamide; (2S)-2α,3α-bis-methoxycarbonyloxy-4β-[N6-[2-(5-chloro-2-thienyl)-(1R)-1-methylethyl]amino-9-adenyl]cyclopentane-1β-N-ethyl-carboxamide; (2S)-2α,3α-dihydroxy-4β-[N6-[2-(5-chloro-2-thienyl)-(1R)-1-methylethyl]amino-9-adenyl]-cyclopentane-1β-N-ethylcarboxamide ethoxymethylene acetal; (2S)-2α,3α-dihydroxy-4β-[N6-[2-(5-chloro-2-thienyl)-(1R)-1-methylethyl]amino-9-adenyl]cyclopentane-1β-N-ethylcarboxamide-2,3-carbonate; (2S)-2α,3α-bis-methylcarbamoyloxy-4β-[N6-[2-(5-chloro-2-thienyl)-(1R)-1-methylethyl]amino-9-adenyl]cyclopentane-1β-N-ethylcarboxamide; (2S)-2α,3α-dihydroxy-4β-[N6-[2-(5-chloro-2-thienyl)-(1R)-1-methylethyl]amino-9-adenyl]cyclopentane-1β-N-ethylcarboxamide-2,3-thiocarbonate; $N^6$-[2-(3-chloro-2-thienyl)-(1R)-1-methylethyl]-2'-O-methyladenosine; $N^6$-[2-(5-chloro-2-thienyl)-(1R)-1-methylethyl]-2'-O-methyladenosine; and $N^6$-[trans-5-(2-thienyl)cyclohex-1-en-4-yl]-2'-O-methyladenosine.

A preferred class of compounds of the invention is described by Formula I wherein R' and R'' are H.

Another preferred class of compounds of the invention are the 5'-N-alkylcarboxamide derivatives of the N6-heterocyclic-substituted carbocyclic adenosines, in other words, the compounds of Formula I, wherein K is N, Q is CH$_2$ and T is R$_1$R$_2$N—C≡O, or pharmaceutically acceptable salts thereof.

Still another preferred class of compounds of the invention are the 5'-N-alkylcarboxamide derivatives of the N6-heterocyclic-substituted-N'-1-deazaaristeromycins, i.e., the 4-[7-[heterocyclylamino]-3H-imidazo[4,5-b]pyridin-3-yl]-alkyl-2,3-dihydroxycyclopentanecarboxamides, in other words, the compounds of Formula I, wherein K is CH, Q is CH$_2$, and T is R$_1$R$_2$N—C≡O, or pharmaceutically acceptable salts thereof.

The most preferred class of compounds of the invention comprise the compounds of Formula I characterized by the presence of a chiral center alpha to the N6 atom of the purine or 1-deazapurine ring, while a special embodiment of this class includes compounds characterized by a chiral ethyl group attached to the carbon atom alpha to the N6-nitrogen. A particularly preferred class of compounds are characterized by an N6-[1-loweralkyl-2-(3-halothien-2-yl)ethyl]substituent group.

Most preferred embodiments of the invention comprise the compounds (-)-[2S-[2α,3α-dihydroxy-4β-[N6-[2-(5-chloro-2-thienyl)-1-(R)-methylethyl]-amino]-9-adenyl]cyclopentane-1β-ethylcarboxamide, (−)-[2S-

[2α,3α-dihydroxy-4β-[N6-[1-(R)-ethyl-2-(3-chloro-2-thienyl)ethyl]amino]-9-adenyl]cyclopentane-1β-ethyl-carboxamide, [1S-[1α,2β,3β,4α(S*)]]-4-[7-[[2-(5-chloro-2-thienyl)-1-methylethyl]amino]-3H-imidazo[4,5-b]pyridin-3-yl]-N-ethyl-2,3-dihydroxycyclopentanecarboxamide, and pharmaceutically acceptable salts thereof.

Compounds of this invention may be prepared by known methods or in accordance with the reaction sequences described below. The starting materials used in the preparation of compounds of the invention are known or commercially available, or can be prepared by known methods or by specific reaction schemes described herein.

Compounds of Formula I, wherein K is N, Q is O and T is $R_3O-CH_2$, may be prepared by reacting commercially-available 6-chloropurine riboside with various heterocyclic amines as exemplified below.

Compounds of Formula I, wherein K is N, Q is O and T is $R_1R_2N-C\!=\!O$ are similarly prepared starting with the product of Reaction Scheme A. In this reaction, 6-chloropurine riboside, with the 2'- and 3'- hydroxyl groups of the ribose ring protected, is treated with an oxidant, for example a Jones reagent, and the product acid treated with either dicyclohexlcarbodiimide (DCC) or BOP-Cl in the presence of a selected amine, to yield the 5'-alkylcarboxamide derivative.

REACTION SCHEME A

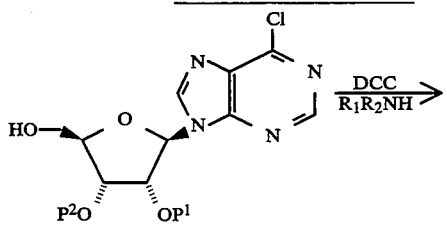

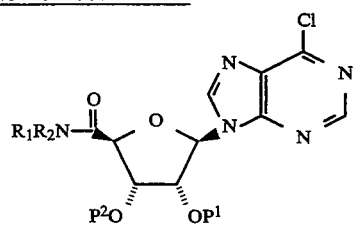

(P = protecting group)

Suitable starting materials for compounds of Formula I wherein K is N, Q is $CH_2$ and T is $R_1R_2N-C\!=\!O$, may be prepared as described by Chen et al., Tetrahedron Letters 30: 5543-46 (1989). Alternatively, Reaction Scheme B may be used to prepare such starting materials. In carrying out Reaction Scheme B, the 4-ethylcarboxamide derivative of 2,3-dihydroxycyclopentylamine, prepared as described by Chen et al., is reacted with 3-amino-2,4-dichloropyrimidine. The product of this initial reaction is then heated with an aldehydylamidine acetate, for example formamidine acetate in dioxane and methoxyethanol, for a time sufficient to effect ring closure (from about 30 min to about 4 hours), thereby yielding a product which may be conveniently reacted with various heterocyclic amines in the manner described below, to give the compounds of the invention. The order of reaction is not critical. For example, the intermediate formed in Reaction Scheme B could be reacted with a heterocyclic amine, followed by ring closure to yield the desired final product.

REACTION SCHEME B

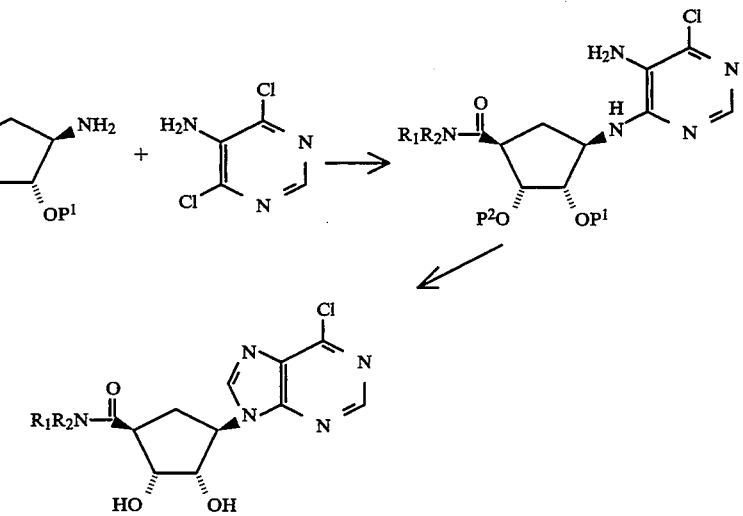

Various heterocyclic amines, useful in forming the compounds of this invention, may be prepared by one or more of the reactions shown in Reaction Schemes C-J and preparative Examples B through G, and 50 through 74, hereinbelow (Het=heterocyclic group; Halo=halogen; R=e.g. H or lower alkyl; $R_a$ and Y are as previously described).

REACTION SCHEME C
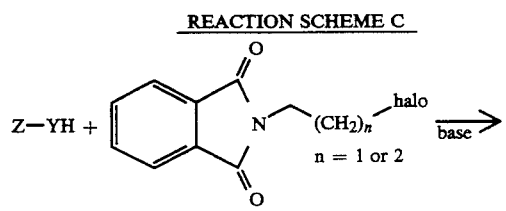
REACTION SCHEME E
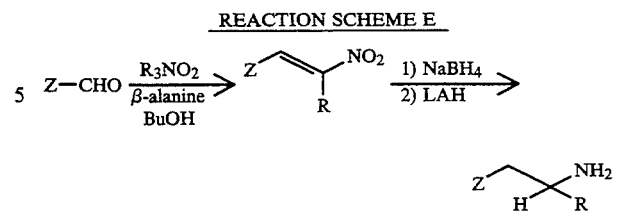
REACTION SCHEME F
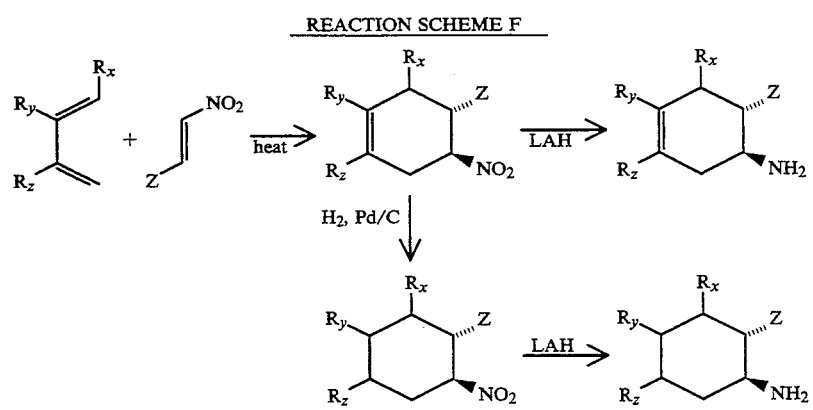
REACTION SCHEME G
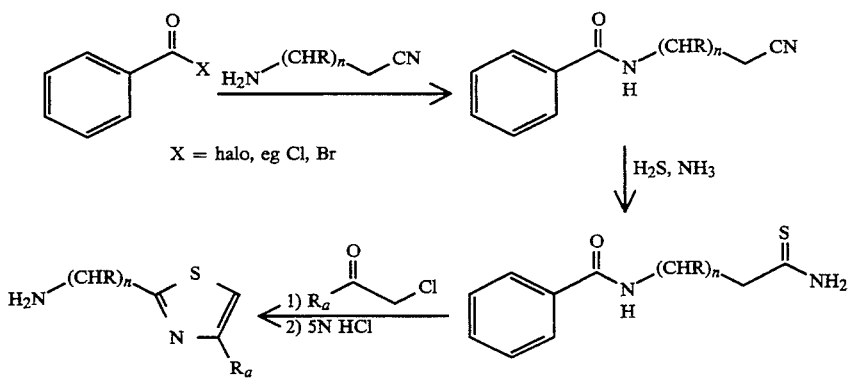
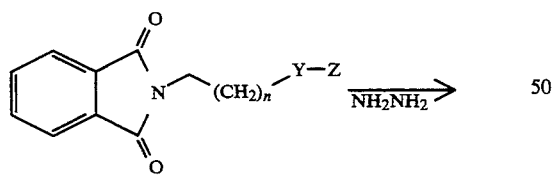
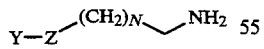
REACTION SCHEME D
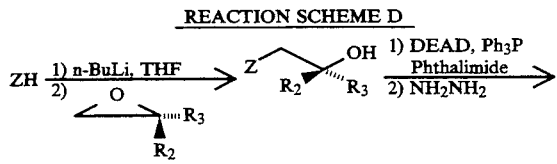
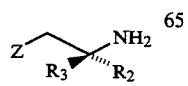
REACTION SCHEME H
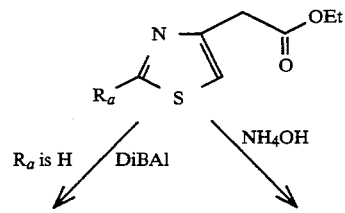

-continued
REACTION SCHEME H

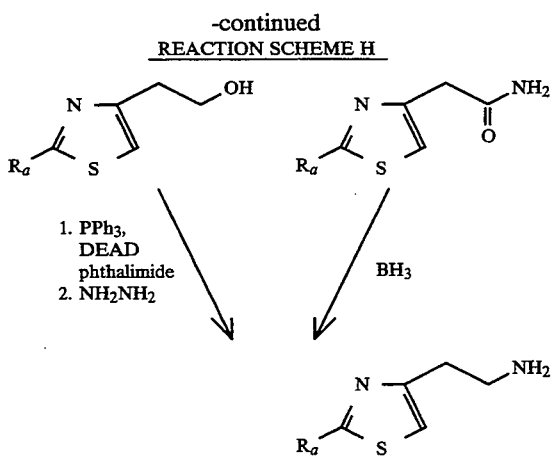

REACTION SCHEME I

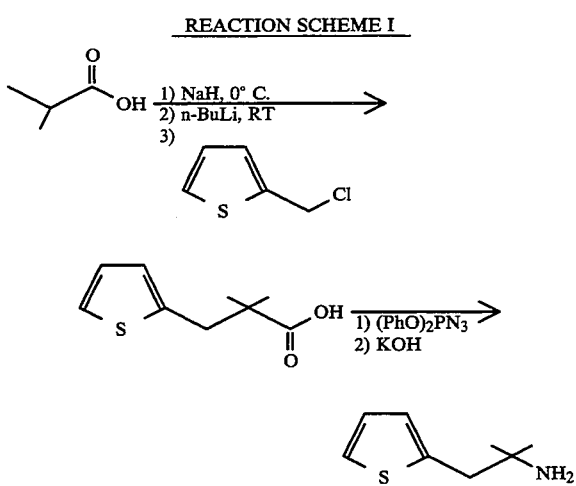

The reaction sequence of Scheme I above is described in U.S. Pat. No. 4,321,398, with pertinent information incorporated herein by reference.

EXAMPLE B

Preparation of 1-(thiophen-3-yl)ethylamine

3-Thiophencarboxaldehyde (1 mmole), nitromethane (1.5 mmole) and beta-alanine (0.1 mmole) in butanol for 6 hours to give 3 -nitrovinylenethiophene, which is reduced with lithium aluminum hydride (2.5 mmole) to yield the desired product amine.

3-Substituted thienylalkylamines are prepared by substituting 3-substituted thiophenes, such as 3-chlorothiophene, for the thiophene starting materials in Example B above.

EXAMPLE C

Preparation of trans-2-(thiophen-2-yl)cyclohex-4-enylamine

A mixture of 1,3-butadiene (5 ml) and 2-nitrovinylenethiophene (7 g) in toluene is heated at 140° C. overnight in a sealed tube. The resulting nitrocyclohexene is hydrogenated (~35 psi H$_2$) (5% Pd/C MeOH) and treated with lithium aluminum hydride (2.5 g). The racemic trans-2-(thiophen-2-yl)-cyclohexylamine is obtained with a standard workup.

EXAMPLE D

General Preparation of 2-substituted Thiazole Amines

Benzoyl chloride and aminoethylcyanide are reacted to give N-benzoylaminoethylcyanine, which is reacted with hydrogen sulfide in ammonia to yield the thioamide, which is reacted with an appropriate α-halo ketone to yield the desired thiazole. Treatment with 5N hydrochloric acid removes the protecting benzoyl group to give the desired amine product.

EXAMPLE E

General Preparation of 4-Substituted Thiazolyl Amines

A preferred synthesis for 2-(2'-methyl-4'-thiazolyl)ethylamine is by reacting thioacetamide with ethyl monobromoacetoacetate to give a thiazole ester which is reduced preferably with sodium borohydride to yield the alcohol which is converted to the amine. A preferred means to the amine comprises treatment with (i) diethylazodicarboxylate, triphenylphospine and phthalimide and (2) hydrazine hydrate.

The preparation of 4-substituted thiazole amines may also be carried out by using the foregoing reaction scheme by reacting a substituted thioamide and ethylmonobromoacetoacetate. Conversion of the resulting thiazolyl ester to the amide is effected with aqueous ammonia and the amine is formed by reduction with borane. An exemplary preparation of 2-(1,1-dimethyl-1'-thiophenyl)ethylamine is described in U.S. Pat. No. 4,321,398.

Diastereomeric mixtures of compounds or intermediates obtained in Reaction Schemes A–I above may be separated into single racemic or optically active enantiomers by methods known in the art; for example, by chromatography, fractional distillation or fractional crystallization of d- or l-(tartarate, dibenzoyltartarate, mandelate or camphorsulfonate) salts.

EXAMPLE F

Preparation of (+) and (−) trans-2-(thiophen-2-yl)cyclohex-4-enylamine (S)-(+)-Mandelic acid (0.55 eq) is added to an isopropanol solution of the racemic amine (3.4 g) prepared in Example C. The precipitate is recrystallized from isopropanol to provide 1.78 g of the salt ([α]$_D$RT= +4.13 (C=1.3, MeOH)). The amines are isolated by extracting the neutralized salts (sat. NaHCO$_3$) with CH$_2$Cl$_2$, drying (Na$_2$SO$_4$) and concentrating to provide the free amines partially resolved.

Approximately 1 g of the levorotatory amine ([α]$_D$RT= −25.8 (c=1.54, MeOH)) is treated with 2 g of l-(−)-dibenzoyl tartaric acid in methanol and the resulting salt is worked up to provide 0.64 g of the levorotatory amine ([α]$_D$RT= −28.8 (c=1.65, MeOH)). High-field NMR analysis of the MPTA amide of the levorotatory amine revealed >96% enantiomeric excess.

Approximately 1.6 g of the enriched dextrorotatory amine mixture is treated with 3.2 g of d(+)-dibenzoyl tartaric acid in methanol. After workup, 0.87 g of the dextrorotatory amine is obtained ([α]$_D$RT= +25.8 (c=1.67, MeOH)).

The N6-heterocyclic-substituted adenosines and carbocyclic adenosines of the invention may be formed by reacting 6-chloropurine riboside or the products of Reactions Scheme A or B with various heterocyclic amines, according to the synthetic route shown below in Reaction Scheme J, wherein K, P, Q and T are as previously defined.

REACTION SCHEME J

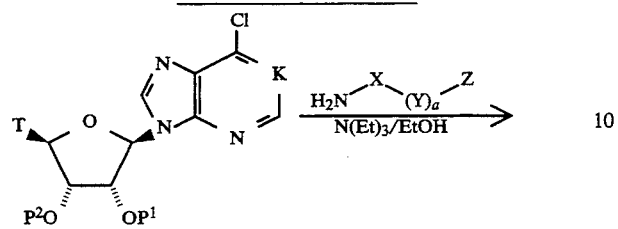

The N6-heterocyclic-substituted-N'alkyl-deazaaristeromycins of the invention may be prepared as shown in Reaction Scheme K.

REACTION SCHEME K

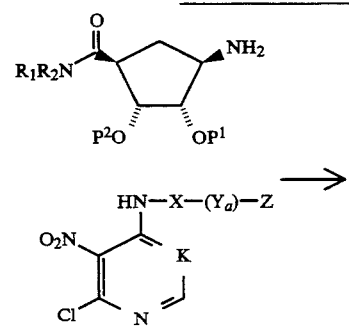

-continued
REACTION SCHEME K

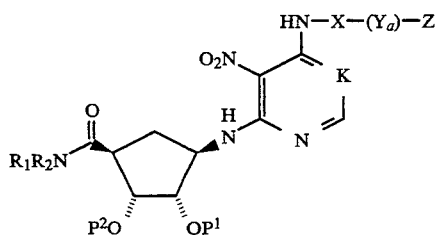

1) Pd/C, H$_2$ or SnCl$_2$
2) formamidine acetate
3) deprotect

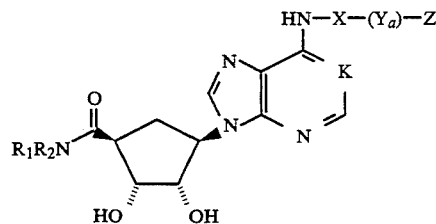

Compounds of the present invention which may act as pro-drugs include those compounds wherein the hydroxyl groups on the ribose or cyclopentane ring are substituted with groups R' and R" as defined above for Formula I.

These may be prepared by known methods and are exemplified by the preparations shown in Reaction Scheme L, below.

REACTION SCHEME L

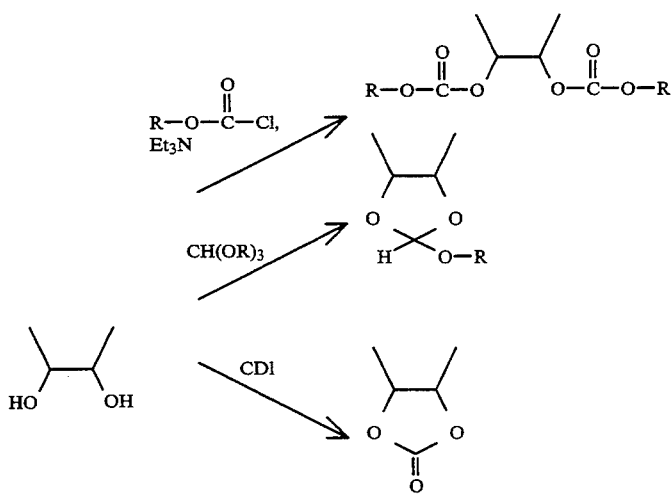

REACTION SCHEME L

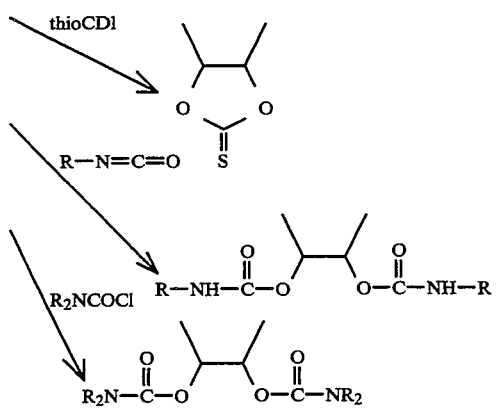

Treatment of the dihydroxy compounds with a chloroformate ester in the presence of an organic base, for example triethylamine, will give the corresponding bis-carbonate. The alkoxymethylene acetal may be prepared by treatment with the corresponding orthoester in the presence of a catalytic amount of p-toluenesulfonic acid. The carbonate is available by treatment with 1,1'-carbonyldiimidazole and the thiocarbonate by treatment with thiocarbonyldiimidizole. The alkyl and dialkylcarbamoyl derivatives may be prepared by treatment with the corresponding alkyl isocyanate or dialkyl carbamoyl chloride in the presence of an organic base respectively.

Compounds of the present invention wherein K is N→O, i.e. the N-oxides, may be prepared by oxidation of the corresponding adenosine or carbocyclic adenosine by known methods, for example by treatment with hydrogen peroxide in acetic acid.

The 2'-O-alkyl derivatives may be prepared by known methods, for example by reaction of the appropriate heterocyclyl amine with 6-chloro-9-(2'-O-methyl-$\beta$-D-ribofuranosyl)-9H-purine.

Functional groups of starting compounds and intermediates that are used to prepare the compounds of the invention may be protected by common protecting groups known in the art. Conventional protecting groups for amino and hydroxyl functional groups are described, for example, in T. W. Greene, "Protective Groups in Organic Synthesis", Wiley, New York (1984).

Hydroxyl groups may be protected as esters, such as acyl derivatives, or in the form of ethers. Hydroxyl groups on adjacent carbon atoms may advantageously be protected in the form of ketals or acetals. In practice, the adjacent 2' and 3' hydroxyl groups of the starting compounds in Reaction Schemes A and B are conveniently protected by forming the 240,3' isopropylidene derivatives. The free hydroxyls may be restored by acid hydrolysis, for example, or other solvolysis or hydrogenolysis reactions commonly used in organic chemistry.

Following synthesis, compounds of the invention are typically purified by medium pressure liquid chromatography (MPLC), on a chromatotron, radially accelerated thin layer chromatography, flash chromatography or column chromatography through a silica gel or Florsil matrix, followed by crystallization. For compounds of Formula I wherein K is N, Q is O and T is $R_3O$—$CH_2$, typical solvent systems include chloroform:methanol, ethyl acetate:hexane, and methylene chloride:methanol. Eluates may be crystallized from methanol, ethanol, ethyl acetate, hexane or chloroform.

For compounds of Formula I, wherein K is N, Q is O and T is $R_1R_2N$—C=O, typical solvent systems include chloroform:methanol. Eluates may be crystallized from 50–100% ethanol (aqueous).

For compounds of Formula I, wherein Q is $CH_2$, K is N or CH, and T is $R_1R_2N$—C=O, typical solvent systems include methylene chloride:methanol. Eluates may be crystallized from ethyl acetate with or without methanol, ethanol or hexane.

Compounds requiring neutralization may be neutralized with a mild base such as sodium bicarbonate, followed by washing with methylene chloride and brine. Products which are purified as oils are sometimes triturated with hexane/ethanol prior to final crystallization.

A further aspect of the present invention relates to an improved method for preparing a substantially optically pure 2-substituted-2-amino-1-(heteroar-2' or 3-yl) ethane derivative. 2-(Heteroaryl)ethylamines and alkyl and phenyl derivatives thereof have been prepared by a variety of means including reduction of 2-$\beta$-nitrovinylheteroaryl compounds prepared from the heteroarylformaldehydes (see, e.g., W. Foye and S. Tovivich, J. Pharm. Scien. 68 (5), 591 (1979), S. Conde, et al., J. Med. Chem. 21 (9), 978 (1978), M. Dressier and M. Joullie, J. Het. Chem. 7, 1257 (1970)); reduction of cyanomethylheteroaryl compounds (see, e.g., B. Crowe and F. Nord, J. Org. Chem. 15, 81 (1950), J. McFarland and H. Howes, J. Med. Chem. 12, 1079 (1969)); Hoffman degradation reaction of 2-(2-thienyl)propyl amide (see, e.g., G. Barger and A. Easson, J. Chem. Soc. 1938, 2100); and amination of 2-(2-thienyl)ethylparatoluenesulfonates, U.S. Pat. No. 4,128,561.

The present method comprises reacting a chiral 2-substituted ethylene oxide derivative with a 2' or 3-yl anion of a heteroaryl compound, and converting, by stereospecific means, the hydroxy group formed in said reaction to an amino group. The method of the present invention is shown in Reaction Scheme M below.

REACTION SCHEME M

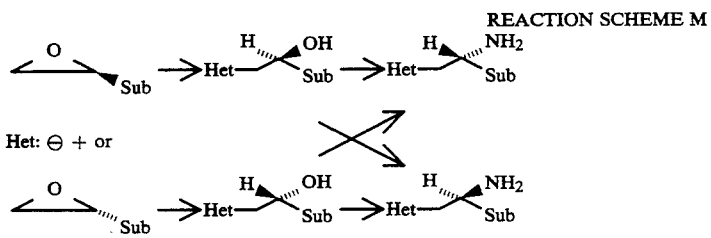

Where Sub represents a substituent group on said chiral ethylene oxide and Het represents a heterocyclic group.

An advantage of the method of the present invention over methods of preparation of 2-substituted-2-amino-1-(heteroar-2- or 3-yl) ethane derivatives known in the art is that of preparation of a substantially optically pure derivative directly as contrasted with that of a racemic mixture which must then be resolved by other methods to yield the optically pure isomers.

A preferred class of the method of the present invention is that in which the heteroar-2- or 3-yl group is a substituted or unsubstituted thien-2- or 3-yl or a substituted or unsubstituted benzothiophen-2- or 3-yl group.

A more preferred class of the method of the present invention is that in which said anion is formed by reacting a substituted or unsubstituted thiophene or benzothiophene having a hydrogen substituent in the 2- or 3-position with an organometallic base in an aprotic organic solvent.

Another more preferred class of the method of the present invention is that in which said chiral 2-substituted ethylene oxide is substituted in the 2-position by a group selected from the group consisting of alkyl, aryl, trihalomethyl, and benzyloxy.

A most preferred class of the method of the present invention is that in which said organometallic base is an alkyllithium or lithium diisopropylamide, said aprotic organic solvent is tetrahydrofuran, ether, hexane, or a mixture of those solvents, and said chiral 2-substituted ethylene oxide is a 2-alkyl ethylene oxide derivative.

Means for stereospecifically converting a hydroxy group to an amino group are well known in the art (see, e.g., Mitsunobu, Synthesis 1981 (1), 1).

It should be apparent that the (R)- or (S)-2-substituted-2-hydroxy-1-heteroarylethane derivative may be formed directly as described above by use of the corresponding (S)- or (R)-2-substituted ethylene oxide derivative as the starting material or, if desired or necessary, a resulting (R) or (S)-2-substituted-2-hydroxy-1-heteroarylethane could be converted to the corresponding (S) or (R)-2-substituted-2-hydroxy-1-heteroarylethane derivative, respectively, by means, well known in the art, for inverting the configuration at the hydroxy group (see, e.g., Mitsunobu, Synthesis 1981 (1), 1).

A specific embodiment of the method of the present invention is that in which: (a) a substituted or unsubstituted thiophene or benzothiophene having a hydrogen substituent in the 2- or 3- position is treated with butyllithium in a mixture of tetrahydrofuran and hexanes at a reduced temperature, for example about −30° C., for a time sufficient to form the anion of said thiophene or benzothiophene; (b) thereafter an (S) or (R) 2-alkyl ethylene oxide is added and the mixture held at a higher temperature, for example about 0° C., for a time sufficient to form the corresponding (R) or (S) 2-alkyl-2-hydroxy-1-thienyl or benzothiophenyl ethane derivative; and (c) thereafter converting, by a stereospecific means, the hydroxy group of said ethane derivative to an amino group.

The method of the present invention is further illustrated and explained by Examples 50 through 74 hereinbelow.

Examples 1–3 describe the preparation of precursor compounds used in the preparation of compounds of the present invention which are described below.

EXAMPLE 1

Preparation of 6-Chloro-2',3'-dimethylmethylenedioxy-N-5'-ethyl carboxamido adenosine Step 1: 2',3'-dimethylmethylene derivative of 6-chloropurine riboside 6-Chloropurine riboside (31.5 g), triethylorthoformate (73 ml) and TsOH (19.8 g) are stirred in 600 ml acetone for 2 hours at RT. The solution was reaction mixture is concentrated in vacuo, combined with ethyl acetate and washed with saturated NaHCO$_3$ solution, and brine, dried (Na$_2$SO$_4$) and concentrated to yield the 2',3'-dimethylmethylene derivative of 6-chloropurine riboside as a white solid.

Step 2: 6-Chloro-2',3' dimethylmethylenedioxy adenosine-5'-carboxylic acid

The product of Step 1 (10 g) is subjected to a Jones oxidation, the acid extracted from ethyl acetate with 2.5% NaOH solution, and the aqueous portion washed with ethyl acetate and acidified with concentrated HCl and extracted with ethyl acetate. The organic layer is washed with H$_2$O and brine, dried (Na$_2$SO$_4$), filtered and concentrated in vacuo to dryness, yielding the desired 5'-carboxylic acid.

Step 3: 6-Chloro-2',3'-dimethylmethylenedioxy-N-5'ethyl carboxamido adenosine

The product from Step 2 (5.7 g) is stirred with BOP-Cl (Bis-(2-oxo-3-oxazoladinyl) phosphinic chloride) (4.26 g) and triethylamine (2.33 ml) in 100 ml methylene chloride for 20 min at RT. Ethylamine (3.46 g) is stirred into the solution which is stirred for 2 hours at RT. The organic portion is washed with diluted HCl solution, dilute NaOH, H$_2$O, brine and dried (Na$_2$SO$_4$) to yield the final product as a foam.

EXAMPLE 2

Preparation of (+)-2S-[2α,3α-dimethylmethylenedioxy]-4β-[6-chloro-9-adenyl]cyclopentane-1-β-N-ethyl carboxamide Step 1: 5,6-Dimethylenedioxy-2-azabicyclo[2.2.1]heptan-3-one 5,6-Dihydroxy-2-azabicyclo[2.2.1]heptan-3-one (23.5 g), (Aldrich) or prepared according to the procedure of Cermak and Vince, Nucleic Acid Chemistry, Improved and New Synthetic Procedures, Methods and Techniques, Part Three, page 26 (J. Wiley 1986), is dissolved in acetone (150 ml) containing 2,2-dimethoxypropane, (185 ml) and p-toluenesulfonic acid (5.25 g), and the mixture is refluxed for 10 min, cooled, treated with NaHCO$_3$ (9.3 g) and concentrated in vacuo. The residue is dissolved in CH$_2$Cl$_2$, washed with brine, dried over MgSO$_4$ and the solvent evaporated to yield a oil. The oil is chromatographed SiO$_2$(4:1, ethyl acetate hexane) to give 17.0 g (63%) of a tan white solid. (mp 153°–154° C.).

Step 2:(+)-4$\beta$-amino-2$\alpha$,3$\alpha$-dimethylenedioxycyclopentane-1$\beta$-N-ethyl carboxamide (A) 5,6-Dimethylenedioxy-2-azabicyclo[2.2.1]heptan-3-one (5 g), prepared in Step 1, is treated with ethylamine (15 ml) at 140° C. for about 7 hours. The resulting product is purified by flash chromatography (CH$_2$Cl$_2$/CH$_3$OH/N,N-dimethyl ethylamine, (90/7/3) to yield (±)4$\beta$-amino-2$\alpha$,3$\alpha$-dimethylenedioxy cyclopentane-1$\beta$-ethylcarboxamide (5.8 g).

(B) Treatment of the racemic amine (13.1 g), prepared as described in part A, with D-dibenzoyltartaric acid (21.6 g) affords 15.1 g of an enantiomerically pure salt, $[\alpha]_D$RT= +70.1 (C. 1.77, CH$_3$OH). The salt is dissolved in 10% aqueous NaOH and the aqueous phase is extracted with ethyl acetate. The combined organic layers are washed with brine, dried over MgSO$_4$ and the solvent removed to afford the optically pure compound. $[\alpha]_D$RT= +31.4[C. 1.40, MeOH]

Step 3: 4-$\beta$-(3-amino-4-chloro-2-pyrimidinylamino)-2,3-dimethylenedioxycyclopentane-1$\beta$-N-ethyl-carboxamide Condensation of (+) 4$\beta$-amino-2$\alpha$,3$\alpha$-dimethylenedioxycyclopentane-1$\beta$-N-ethyl carboxamide (2.10 g), prepared in Step 2, part B, with 3-amino-2,4-dichloropyridine (1.5 g) in n-butanol (70 ml) containing triethylamine (3 mi) for about 14 hours at reflux followed by removal of solvent in vacuo affords an oil which is dissolved in ethyl acetate and washed with aqueous NaHCO$_3$. The organic extract is dried over Na$_2$SO$_4$ and concentrated in vacuo to yield the optically pure compound. $[\alpha]_D$RT= +15.8(C.41.48, CH$_3$OH)

Step 4: (+)-4$\beta$-(3-amino-4-chloro-2-pyrimidinylamino)-2$\alpha$,3$\alpha$-dimethylene dioxycyclopentane (2.10 g), formamdine acetate (1.85 g) in methoxyethanol (2 ml) and dioxane (80 ml) are stirred at 70° C. for about 3 hours. The mixture is cooled to room temperature and the solvent removed in vacuo. The residue is dissolved in ethyl acetate which is washed with aqueous NaHCO$_3$ and brine, the organic extract is dried over Na$_2$SO$_4$, concentrated in vacuo and purified by flash column chromatography (methylene chloride/methanol 95:5) to yield pure (+)-[2$\alpha$,3$\alpha$-dimethylmethylenedioxy]-4$\beta$-[6-chloro-9-adenyl]cyclopentane-1$\beta$-N-ethyl carboxamide (1.45 g).

Alternatively, optically pure 2$\alpha$,3$\alpha$-diprotected dioxy-4$\beta$-6-substituted-9-adenyl-cyclopentane-1$\beta$-N-ethyl carboxamide derivatives can be prepared by the reaction scheme exemplified in Example 3.

EXAMPLE 3

Preparation of 2S-[2$\alpha$,3$\alpha$-cyclohexylidene dioxyl]-4$\beta$-[N6-(2-thienethan-2yl)-9-adenyl]cyclopentane-1$\beta$-N-ethyl carboxamide Step 1: 4$\beta$-ethylene-2$\alpha$,3$\alpha$-[cyclohexylidenedioxy]cyclopentanone (−)-2$\alpha$,3$\alpha$-[Cyclohexylidenedioxy]-4-cyclopentanone, (2.95 g), prepared following the procedure of Borchardt et. al. J. Org. Chem. 1987, 52, 5457, is added as a solution in THF (5 ml) to a mixture of vinyl magnesium bromide (15.2 mmol) and CuI (15.2 mmol) in THF (100 ml). This mixture is maintained at −78° C. under an inert atmosphere for about 2 hours, warmed to 0° C. and quenched with saturated aqueous NH$_4$Cl. The organic phase is washed with brine, dried over MgSO$_4$ and concentrated in vacuo to leave a yellow oil, which is purified by flash chromatography (methylene chloride, 100%) to yield 2.9 g of the desired compound as an oil.

Step 2: 4$\beta$-ethylene-1-$\beta$-hydroxy-2$\alpha$,3$\alpha$-[cyclohexylidenedioxy]cyclopentane 3.95 ml of a 1M solution of diisobutyl aluminum hydride in Tetrahydrofuran is added to a solution of THF(75 ml) and ketone prepared in Step 1 (0.73 g), which is cooled to −78° C. The mixture is warmed to −40° C. for about 2.5 hours, treated with 2N NaOH (5 ml), warmed to room temperature and stirred for about 1.5 hours. The aqueous phase is extracted with diethyl ether, and the combined organic phases are washed with brine, dried over MgSO$_4$ and concentrated in vacuo to a yellow oil which is purified by flash column chromatography (methylene chloride/methanol, 95:5) to yield 0.65 g of pure product as a viscous oil.

Step 3: 4$\beta$-ethylene-1$\beta$-trifluoromethanesulfonyl-2,3-[cyclohexylidenedioxy]cyclopentane A solution of 4$\beta$-ethylene-1$\beta$-ethylene-1$\beta$-hydroxy-2$\alpha$,3$\alpha$-[cyclohexylidenedioxy]-cyclopentane (0.65 g) in methylene chloride (5 ml) and pyridine (0.24 ml) is added to a stirred solution of trifluoromethyl sulfonyl anhydride (0.49 ml) in methylene chloride (25 ml) at 0° C. under argon. After about 20 min., brine is added to the reaction mixture, the organic phase is dried over Na$_2$SO$_4$ and the solvent is removed in vacuo to yield the desired product as an orange oil, which is used without further purification.

Step 4: 1-$\beta$-ethylene-[2$\alpha$,3$\alpha$-cyclohexylidenedioxy]-4-$\beta$-[N6-(2-thienylethane-2-yl)9-adenyl]cyclopentane A solution of N6-thiophenylethyl purine (2.13 g), NaH (50% oil dispersion, 0.35 g) and 18-crown-6 (0.15 g) in DMF (60 ml) is added to a solution of 4$\beta$-ethylene-1$\beta$-trifluoromethylsulfonyl-2$\alpha$,3$\alpha$-[cyclohexylidenedioxy]cyclopentane, prepared in step 4, in DMF (2 ml) at 0° C. The mixture is stirred at 0° C. for about 8 hours, quenched with saturated NH$_4$Cl, the solvent removed in vacuo, and the residue combined with ethyl acetate (100 ml) and brine. The organic layer is dried over MgSO$_4$ and concentrated in vacuo, and the crude product purified by flash chromatography (methylene chloride/methanol (99:1)) to yield 0.85 g of pure product.

Step 5: 2S[2$\alpha$,3$\alpha$-cyclohexylidenedioxy]-4$\beta$-[N6-(2-thienylethan-2-yl)-9-adenyl]cyclopentane-1-$\beta$-N-ethyl carboxamide A solution of 1$\beta$-ethylene-[2$\alpha$,3$\alpha$-cyclohexylidenedioxy]-4-$\beta$-[N6-(2-thienylethane-2-yl)-9-adenyl]cyclopentane (0.32 g) in 2 ml of benzene is added to a benzene solution of potassium permanganate (0.29 g) and 18-crown-6 (0.016 g) at 0° C. The reaction mixture is maintained at room temperature for about 6 hours, 5% aqueous NaOH (15 ml) added and the aqueous phase filtered through Celite ®, and acidified to pH 5 with 1N HCl, and extracted with ethyl acetate. The organic extracts is dried over MgSO$_4$ and concentrated in vacuo to yield 0.1 g of ]2$\alpha$,3$\alpha$-cyclohexylidenedioxy]-4$\beta$-]N6-(2-thienylethan-2-yl)-9-adenyl]cyclopentane-1-$\beta$-carboxylate as a yellow oil which is dissolved in methylene chloride (4 ml) containing dicyclohexyl carbodimide (DCC) (0.044 g). Ethylamine (0.4 ml) is added to the mixture which is allowed to stir at room temperature for about 18 hours, the solvent removed in vacuo and the crude product purified by flash chromatography (methylene chloride/methanol 98:2) to yield 0.077 g of pure product.

EXAMPLE 4

Preparation of
N6-[trans-2-(thiophen-2-yl)cyclohex-4-en-yl adenosine

Trans-2-(2'-thiophenyl)-cyclohex-4-enylamine (0.3 g) prepared according to method described in Example C, above, 6-chloropurine riboside (0.28 g) and triethylamine (0.27 ml) in 20 ml ethanol are heated to reflux overnight under argon. The reaction mixture is cooled to RT, the solvent removed, and the residue purified by MPLC (chloroform:methanol; 95:5), followed by drying in vacuo at approximately 80° C., to yield the final product as a solid, M.P. 105°-110° C.; elemental analysis, $C_{20}H_{23}N_5O_4S$.

EXAMPLE 5

Preparation of
N6-[trans-2-(thiophen-2-yl)cyclohex-4-en-1-yl]adenosine-5'-N-ethylcarboxamide Step 1: (+)Trans-2-(thiophen-2-yl)cyclohex-4-enylamine and the 2',3'-dimethylmethylenedioxy derivative of 6-Cl-NECA are reacted under the conditions described in Example 4, to yield the 2',3'-dimethylmethylenedioxy derivative of the final product.

Step 2: The 2',3'-dimethylmethylenedioxy derivative of the desired product is mixed with trifluoroacetic acid/water (90/110) for 30 min at RT, is neutralized by slowly pouring the mixture into a saturated sodium bicarbonate solution, and is extracted with methylene chloride. The aqueous layer is extracted with methylene chloride and the organic layers combined, washed with brine, dried over magnesium sulfate and filtered, and the filtered clear solution evaporated. The residue is purified by flash chromatography (methylene chloride:-methanol 9:1) to yield, upon drying in vacuo, the final product as a white glassy foam, M.P. 112°-117° C.; $C_{22}H_{26}N_6O_4S$.

EXAMPLE 6

Preparation of
(−)-[2S-[2α,3α-dihydroxy-4-β-[N6-[2-(5-chloro-2-thienyl)-1R)-1-methylethyl]amino]-9-adenyl]cyclopentane]-1-β-N-ethylcarboxamide Step 1:
Optically pure (+)-[2S-[2α,3α-dimethylmethylenedioxy]-4-β-(6-chloro-9-adenyl)]cyclopentane-1-β-N-ethylcarboxamide, prepared as described in Example 2, and 2'R-(5-chlorothien-2-yl)-2-propyl amine, $[α]_DRT = -15.6$ (C. 3.7, $CH_3OH$), prepared as described in Example 4, are combined as described in Example 4 affording the 2,3-dimethylmethylenedioxy derivative of the final product. Step 2:

The dimethylmethylenedioxy derivative of step (1) is heated in 5 ml of 50% aqueous formic acid to reflux for about 3hours. The cooled reaction mixture is evaporated, toluene added to the solid residue and the solvent evaporated. The residue was dissolved in ethyl acetate, washed with sodium bicarbonate solution and brine, dried, filtered, and evaporated to give, after oven drying overnight, a white solid product (0.240 g), M.P. 188°-4° C.; $C_{20}H_{25}N_6SO_3Cl$, $[α]_DRT = -86.49$ (C. 5.5, MeOH).

EXAMPLES 7-29, 31-34

Following the general procedures of Examples 1 to 6 above, the compounds of the invention set forth in Table 1 were prepared. In Examples 7 through 21, 31 and 32, the heterocyclic amine was reacted with commercially available 6-chloropurine riboside; in Examples 22 and 23, the heterocyclic amine was reacted with N6-chloro-5'-N-ethylcarboxamidoadenosine; and in Examples 24 through 31,33 and 34, the heterocyclic amine was reacted with either (±) or (+)-[2α,3α-dimethyl-methylenedioxy-4-β-(6-chloro-9-adenyl)-cyclopentane-1-β-N-ethylcarboxamide.

TABLE I

| Example/RXN Scheme | Amine | Product | M.P./°C. |
|---|---|---|---|
| 7 (F) | (structure: cyclohexyl-NH2 with thiophene) | $N^6$-[trans-2-(thiophen-2-yl)-cyclohex-1-yl]adenosine | 165–170 |
| 8 (F) | (structure: cyclohexenyl-NH2 with thiophene) | $N^6$-[trans-2-(thiophen-3-yl)-cyclohex-4-en-1-yl]adenosine | 99–105 |
| 9 (C) | (structure: benzothiazole-NH-CH2CH2-NH2) | $N^6$-[2-(2'-aminobenzothiazolyl)ethyl]adenosine | 218–219 |
| 10 (C) | (structure: benzothiazole-S-CH2CH2-NH2) | $N^6$-[2-(2'-thiobenzothiazolyl)-ethyl]adenosine | 149–150 |

TABLE I-continued

| Example/ RXN Scheme | Amine | Product | M.P./°C |
|---|---|---|---|
| 11 (C) | (6-ethoxy-benzothiazol-2-yl)-S-CH2CH2-NH2 | $N^6$-[2-(6'-ethoxyl-2'-thiobenzothiazolylethyl]adenosine | 154–155 |
| 12 (H) | H2N-CH2CH2-(4-methylthiazol-5-yl) | $N^6$-[2-(4'-methylthiazol-5'-yl)-ethyl]adenosine | 202–203 |
| 13 (G) | (thiazol-2-yl)-CH2CH2-NH2 | $N^6$-[2-(2'-thiazolyl)ethyl]-adenosine | 181–183 |
| 14 (H) | H2N-CH2CH2-(2-methyl-thiazol-4-yl) | $N^6$-[2-(2'-methyl-4'-thiazolyl)-ethyl]adenosine | 116–118 |
| 15 (D) | (benzo[b]thiophen-2-yl)-CH2-CH(NH2)-CH3 | $N^6$-[(R)-1-methyl-2-(2'benzo-[b]-thiophenyl)ethyl]adenosine[a] | 133–134 |
| 16 (G) | (4-phenyl-thiazol-2-yl)-CH2CH2-NH2 | $N^6$-[2-(4'-phenyl-2'-thiazolyl)-ethyl]adenosine | 124–126 |
| 17 (I) | H2N-CH(CH3)-CH2-(thiophen-2-yl) | $N^6$-[2-(1,1-dimethyl-2'-thiophenyl)ethyl]adenosine | 172–176 |
| 18 (G) | (4-methyl-thiazol-2-yl)-CH2-NH2 | $N^6$-[2-(4'-methyl-2'-thiazolyl)-methyl]adenosine | 104–105 |
| 19 (G) | (4-phenyl-thiazol-2-yl)-CH2-NH2 | $N^6$-[4-phenyl-2-thiazolyl)-methyl]adenosine | 137–139 |
| 20 (D) | (thiazol-2-yl)-CH2-CH(NH2)-CH3 | $N^6$-[1-(thiazol-2-yl)prop-2-yl]-adenosine | 99–106 |
| 21 (D) | (5-chlorothien-2-yl)-CH2-CH(NH2)-CH2CH3 | $N^6$-[1-(5''-chlorthien-2''-yl)-2-butyl]adenosine | 135–136 |

TABLE I-continued

| Example/ RXN Scheme | Amine | Product | M.P./°C |
|---|---|---|---|
| 22 (F[d]) | [cyclohex-4-en-1-yl with thiophen-2-yl substituent and NH2, trans] | N[6]-[trans-2-(thiophen-2-yl)-cyclohex-4-en-1-yl]adenosine-5-N-ethyl carboxamide[b] | 108–112 |
| 23 (C[d]) | [benzothiazol-2-yl-NH-CH2CH2-NH2] | N[6]-[2-(2'-(aminobenzothia-zolyl)ethyl]adenosine-5-N-ethyl carboxamide | 123–124 |
| 24 (H) | [4-methylthiazol-5-yl-CH=CH-CH2-NH2] | (±)-N[6]-[2-(4''-methyl-5''-thiazolyl)ethyl]carbocyclic adenosine-5'-N-ethyl carboxamide | 92–93 |
| 25 (G) | [thiazol-2-yl-CH2CH2-NH2] | (±)-N[6]-[2-(2''-thiazolyl)ethyl]-carbocyclic adenosine-5'-N-ethyl carboxamide | 170 |
| 26 | [thiophen-2-yl-CH2CH2-NH2] | (−)-N[6]-[(thiopen-2''-yl)ethan-2-yl]carbocyclic adenosine-5'-N-ethyl carboxamide | 185–187 |
| 27 (D) | [(R)-1-(thiophen-2-yl)prop-2-yl-NH2] | (−)-N[6][(R)-1-(thiophen-2-yl)prop-2-yl]carbocyclic adenosine-5'-N-ethyl carboxamide[c] | 85–87 |
| 28 (E) | [thiophen-3-yl-CH2CH2-NH2] | (±)-N[6]-[1-(thiopen)-3-yl)ethan-2-yl]carbocyclic adenosien-5'-N-ethyl carboxamide | 195–198 |
| 29 (C) | [benzothiazol-2-yl-NH-CH2CH2-NH2] | (±)-N[6]-[2-(2'-aminobenzothia-zolyl)ethyl]carbocyclic adenosine-5'-N-ethyl carboxamide | 209–211 |
| 31 (D) | [3-chlorothien-2-yl-CH2-CH(NH2)-ethyl] | N[6]-[1-ethyl-2-(3-chlorothien-2-yl)ethyl]adenosine | 137–139 |
| 32 (D) | [3-chlorothien-2-yl-CH2-CH(NH2)-methyl] | N[6]-[1-methyl-2-(3-chlorothien-2-yl)ethyl]adenosine | 137–139 |
| 33 (D) | [3-chlorothien-2-yl-CH2-CH(NH2)-ethyl] | (−)-[2S-[2α,3α-dihydroxy-4β-[N[6]-[2-(3-chloro-2-thienyl)-1(R,S)-ethylethyl]amino]-9-adenyl]cyclo-pentane-1β-ethyl carboxamide | 88–91 |
| 34 | [3-chlorothien-2-yl-CH2-CH(NH2)-ethyl] | (−)-[2S-[2α,3α-dihydroxy-4β-[N[6]-[2-(3-chloro-2-thienyl)-1(R)-ethylethyl]amino]adenyl]cyclo-pentane-1β-ethyl carboxamide | 95–96 |

[a] optical rotation of alcohol precursor of amine: $[\alpha]^{RT} = +14.9°$ (C.1.27, CH$_3$OH)
[b] optical rotation of amine: $[\alpha]^{RT} = +25.8°$ (C.1.67, CH$_3$OH)
[c] optical rotation: $[\alpha]^{RT} = -15.6°$ (C.3.04, CH$_3$OH)
[d] amine reacted with 2',3'-isopropylidene derivative of N[6]-chloro-5'-N-ethylcarboxamide adenosine; deprotection according to procedure of Example 11.

EXAMPLE 30

Preparation of
(±)-N6-[1-(thiopheny-2-yl)ethan-2-yl]-N'-1-deazaaristeromycin-5'-N-ethyl carboxamide Step 1: 2-chloro-3-nitro-4-[2-(2-thiophenyl)ethyl]aminopyridine A mixture of 2,4-dichloro-3-nitropyridine (1.5 g), 2-aminoethylthiophene (1 g) and triethylamine (5 ml) is heated to reflux in EtOH (60 ml). The reaction mixture is cooled, the solvent evaporated and the residue chromatographed on silica gel (10% hexane/$CH_2Cl_2$) to yield the desired addition product.

Step 2: (±) 1β-N-ethyl carboxamide-2α,3α-isopropylidenedioxy-4β-[2-(3-nitro-4-[2-(2-thiophenyl)ethyl]aminopyridyl)amino]cyclopentane A mixture of the thiophenylamino pyridine of step (1) (1.8 mmoles), (±)-1β-N-ethyl carboxamide-4β-amino-2α,3α-isopropylidenedioxycyclopentane (0.3 g) and triethylamine (0.3 ml) is heated to reflux in nitromethane (15 ml) for about 5 hours. The solvent is removed and the residue taken up in methylene chloride, chromatographed on silica gel (2% methanol/chloroform) affording a solid product which is used as is in the next step.

Step 3: (±) 1β-N-ethyl carboxamide-2α,3α-isopropylidenedioxy-4β-[2-(3-amino-4-[2-(2-thiophenyl)ethyl]aminopyridyl)amino]cyclopentane A mixture of the nitro compound of step (2) (0.39 g), Pd/C (0.01 g) in ethanol (7 ml) is stirred under a hydrogen atmosphere for about 5 hours. The catalyst is filtered and the filtrate, evaporated affording an oil which is purified on florisil (10% methanol/methylkene chloride) to yield the desired product as a solid.

Step 4: (±)-N6-[1-(thiopheny-2-yl)ethan-2-yl]-N'-1-deazaaristeromycin-5'-N-ethyl carboxamide A mixture of the amino compound of step (3) (0.31 g) and formamidine acetate (0.72 g) in methoxyethanol (30 ml) is heated to reflux for about 3 hours. The reaction mixture is cooled, the solvent evaporated and water (5 ml) and formic acid (5 ml) added to the residue. The acidic mixture is heated to 50° C. for about 5 hours, after which the solvent is removed and the residue chromatographed on silica gel (10% methanol/methylene chloride) yielding an oil which is recrystallized from ethyl acetate to the desired product as a crystalline solid, M.P.=155°–156° C.

The optically pure compound is prepared using the + or − enantiomer of the cyclopentane amine in Step (2).

EXAMPLE 35

Preparation of
(2S)-2α,3α-dihydroxy-4β-[N6-[2-(5-chloro-2-thienyl)-(1R)-1-methylethyl]ethyl]amino-9-adenyl]cyclopentane-1β-N-ethylcarboxamide-$N^1$-oxide A solution of 2S-2α,3α-dihydroxy-4β-[N6-[2-(5-chloro-2-thienyl)-(1R)-1-methylethyl]amino-9-adenyl]-cyclopentane-1β-N-ethylcarboxamide (0.25 g) and glacial acetic acid (20 ml) in 30% hydrogen peroxide (1 L) is stirred for 4 days at room temperature and the mixture concentrated in vacuo. The residue is purified by flash chromatography, eluting with 20% methanol in ethyl acetate, followed by stirring with hot methanol and filtering to give the desired product, m.p. > 240° C.

EXAMPLE 36

Preparation of
[1S-[1α,2β,3β,4α(S*)]]-4-[7-[[2-(5-chloro-2-thienyl)-1-methylethyl]amino]-3H-imidazo[4,5-b]pyridin-3-yl]-N-ethyl-2,3-dihydroxycyclopentanecarboxamide Step 1: Preparation of 2-chloro-4-[2-(5-chloro-2-thienyl)-(1R)-1-methylethyl]amino-3-nitropyridine Using essentially the procedure of Example 30, Step 1, and purifying the crude product by flash chromatography, eluting with gradient of 10% to 30% ethyl acetate in heptane, the desired product is prepared from 2-(5-chloro-2-thienyl)-(1R)-1-methylethylamine.

Step 2: Preparation of (−)-1β-N-ethyl-2α,3α-isopropylidenedioxy-4β-[4-[2-(5-chloro-2-thienyl)-(1R)-1-methylethyl]amino-3-nitro-2-pyridyl]amino-cyclopentanecarboxamide 2-chloro-4-[2-(5-chloro-2-thienyl)-(1R)-1-methylethyl]amino-3-nitropyridine (0.68 g), (−)-1β-N-ethyl-2α,3α-isopropylidendioxy-4β-amino-cyclopentanecarboxamide (0.381 g), and triethylamine (0.85 ml) are combined in ethanol (50 ml) and the mixture heated at reflux for about 18 hours. The mixture is concentrated in vacuo and the crude product purified by flash chromatography eluting with 0.5% methanol in methylene chloride to give the desired product.

Step 3: Preparation of (−)-1β-N-ethyl-2α,3α,-isopropylidenedioxy-4β-[3-amino-4-[2-(5-chloro-2-thienyl)-(1R)-1-methylethyl]amino-2-pyridyl]amino-cyclopentanecarboxamide (−)-1β-N-ethyl-2α,3α-isopropylidenedioxy-4β-[4-[2-(5-chloro-2-thienyl)-(1R)-1-methylethyl]amino-3-nitro-2-pyridyl]amino-cyclopentanecarboxamide (0.90 g), and tin(II)chloride dihydrate (2.1 g) are combined in ethanol (20 ml) and the mixture heated at 70° C. for about 30 minutes. The mixture is poured over ice, made slightly alkaline with aqueous sodium bicarbonate, and the aqueous extracted with ethyl acetate. The ethyl acetate solution is dried over magnesium sulfate, filtered, and concentrated in vacuo to give the desired product which is used, without further treatment, for the next step.

Step 4: Preparation of [1S-[1α,2β,3β,4α(S*)]]-4-[7-[[2-(5-chloro-2-thienyl)-1-methylethyl]amino]-3H-imidazo[4,5-b]pyridin-3-yl]-N-ethyl-2,3-dihydroxycyclopentanecarboxamide Using essentially the procedure of Example 30, Step 4, the desired product, m.p. 164°–165° C. is prepared from (−)-1β-N-ethyl-2α,3α-isopropylidenedioxy-4β-[2-(5-chloro-2-thienyl)-(1R)-1-methylethyl]amino-2-pyridyl]amino-cyclopentanecarboxamide.

Using essentially the procedures of Example 30, the compounds of Examples are prepared from the appropriate starting materials.

EXAMPLE 37

[1S-[1α,2β,3β,4α]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide, m.p. 79°–82° C.

EXAMPLE 38

[1S-[1α,2β,3β, 4α]]-4-[7-[[2-(2-thienyl)-1-isopropylethyl]amino]-3H-imidazo[4,5-b]pyridin-2-yl]-N-ethyl-2,3-dihydroxycyclopentanecarboxamide, m.p. 75°–85° C.

EXAMPLE 39

[1S-[1α,2β,3β,4α(S*)]]-4-[7-[[2-(3-chloro-2-thienyl)-1-ethylethyl]amino]-3H-imidazo[4,5-b]pyridin-3-yl[-N-ethyl-2,3-dihydroxycyclopentane-carboxamide, m.p. 75°–78° C.

EXAMPLE 40

[1S-[1α,2β,3β,4α(S*)]]-4-[7-[[2-(2-thienyl)-1-methylethyl]amino]-3H-imidazo[4,5-b]pyridin-3-yl]-N-ethyl-2,3-dihydroxycyclopentane-carboxamide, m.p. 155°–6° C.

EXAMPLE 41

Preparation of
[1S-[1α,2β,3β,4α]]-4-[7-[[2-(5-chloro-2-thienyl)-1-ethylethyl]amino]-3H-imidazo[4,5-b]pyridin-3-yl]-N-ethyl-2,3-dihydroxycyclopentane-carboxamide.

Using essentially the procedures of Example 36, the desired product, m.p. 77°–85° C., is prepared from 2-(5-chloro-2-thienyl)-(1R)-1-ethylethylamine.

EXAMPLE 42

Preparation of
(2S)-2α,3α-bis-methoxycarbonyloxy-4β-[N6-[2-(5-chloro-2-thienyl)-(1R)-1-methylethyl]amino-9-adenyl]-cyclopentane-1β-N-ethylcarboxamide To a solution of (2S)-2α,3α-dihydroxy-4β-[N6-[2-(5-chloro-2-thienyl)-(1R)-1-methylethyl]amino-9-adenyl]-cyclopentane-1β-N-ethylcarboxamide (0.56 g) and triethylamine (0.5 ml) and 4-dimethylaminopyridine (1 mg) in tetrahydrofuran (25 ml) is added methyl chloroformate (0.21 ml) and the solution stirred at room temperature for 1 hour. The mixture is diluted with ethyl acetate, washed with brine, and the organic solution dried over magnesium sulfate, filtered and concentrated in vacuo. The crude product is recrystallized from hexane/ethyl acetate to give the desired product, m.p. 74°–76° C.

Preparation of
(2S)-2α,3α-dihydroxy-4β-[N6-[2-(5-chloro-2-thienyl)-(1R)-1-methylethyl]amino-9-cyclopentane-1β-N-ethylcarboxamide ethoxymethylene acetal A solution of (2S)-2α,3α-dihydroxy-4β-[N6-[2-(5-chloro-2-thienyl-(1R)-1-methylethyl]amino-9-adenyl]-cyclopentane-1β-N- ethylcarboxamide (0.14 g), triethylorthoformate (3 ml), and p-toluenesulfonic acid (1 mg) is heated at reflux for about 1 hour and the solvent and the solvent then removed in vacuo. The residue is dissolved in ethyl acetate and the solution washed with brine, dried over sodium sulfate, filtered, concentrated in vacuo. The crude is purified by flash chromatography, eluting with 5% methanol in methylene chloride, followed by recrystallization from hexane/ethyl acetate to give the desired product, m.p. 67°–70° C.

EXAMPLE 44

Preparation of (2S)-2α,3α-dihydroxy-4β-[N6-[2-(5-chloro-2-thienyl)-(1R)-1-methylethyl]amino-9-adenyl]cyclopentane-1β-N-ethylcarboxamide-2,3-carbonate A solution of (2S)-2α,3α-dihydroxy-4α-[N6-[2-(5-chloro-2-thienyl)-(1R)-1-methylethyl]amino-9-adenyl]-cyclopentane-1β-N-ethylcarboxamide (0.17 g) and 1,1'-carbonyldiimidazole (0.071 g) in benzene (5 ml) is refluxed for 5 hours then stirred at 60° C. for about 18 hours. The solution is washed with brine, dried over magnesium sulfate, filtered and concentrated in vacuo. The residue is purified by flash chromatography, eluting with 5% methanol in methylene chloride, followed by crystallization from hexane/ethyl acetate to give the desired product, m.p. 87°–89° C.

EXAMPLE 45

Preparation of
(2S)-2α,3α-bis-methylcarbamoyloxy-4β-[N6-[2-(5-chloro-2-thienyl)-(1R)-1-methylethyl]amino-9-adenyl]-cyclopentane-1β-N-ethylcarboxamide To a solution of (2S)-2α,3α-dihydroxy-4β-[N6-[2-(5-chloro-2thienyl)-(1R)-1-methylethyl]amino-9-adenyl]-cyclopentane-1β-N-ethylcarboxamide (0.16 g) in tetrahydrofuran (5 ml) is added methyl isocyanate (-.05 ml) and 1,8-diazabicyclo[5.4.0]undec-7-ene (1 drop). The solution is stirred at 50° C. for about 2.5 hours, cooled to room temperature, diluted with ethyl acetate and washed with brine. The organic solution is washed with brine, dried over magnesium sulfate and concentrated in vacuo. The residue is purified by flash chromatography, eluting with 5% methanol in methylene chloride, followed by crystallization from hexane/ethyl acetate to give the desired product, m.p. 97°–99° C.

EXAMPLE 46

Preparation of
(2S)-2α,3α-dihydroxy-4β-[N6-[2-(5-chloro-2-thienyl)-(1R)-1-methylethyl]amino-9-adenyl]cyclopentane-1β-N-ethylcarboxamide-2,3-thiocarbonate A solution of (2S)-2α,3α-dihydroxy-4β-[N6-[2-(5-chloro-2-thienyl)-(1R)-1-methylethyl]amino-9-adenyl]-cyclopentane-1β-N-ethylcarboxamide (0.35 g) and thiocarbonyldiimidazole (0.134 g) in benzene (10 ml) is heated at 45° C. for about 2 hours. The solution is washed with brine, dried over magnesium sulfate, and concentrated in vacuo. The residue is purified by flash chromatography, eluting with 5% methanol in hexane, followed by crystallization from hexane to give the desired product, m.p. 115°–117° C.

EXAMPLE 47

Preparation of
N6-[2-(3-chloro-2-thienyl)-(1R)-1-methylethyl]-2'-O-methyladenosine A solution of 6-chloro-9-(2'O-methylβ-D-ribofuranosyl)-9H-purine (prepared s in EP Publication No. 0378158) (0.28 g), 2-(3-chloro-2-thienyl)-(1R)-1-methylethylamine (0.163 g), and triethylamine (0.5 ml) in ethanol (30 ml) is refluxed for about 18 hours, cooled and concentrated in vacuo. The residue is purified by flash chromatography, eluting with 10% methanol in methylene chloride, followed by crystallization from hexane/ethyl acetate, to give the desired product, m.p. 75°–76° C.

EXAMPLE 48

Preparation of
N6-[2-(5-chloro-2-thienyl)-(1R)-1-methylethyl]-2'-O-methyladenosine Using essentially the procedure of Example 47, the desired product, m.p. 84°–85° C., is prepared from 2-(5-chloro-2-thienyl)-(1R)-1-methylethylamine.

EXAMPLE 49

Preparation of
N6-[trans-5-(2-thienyl)cyclohex-1-en-4-yl]-2'-O-methyladenosine

Using essentially the procedure of Example 47, the desired product, m.p. 86°–89° C., is prepared from trans-2-(2-thienyl)cyclohex-4-enylamine.

EXAMPLE 50

Preparation of
1(R)-2-(5-chloro-2-thienyl)-1-methylethylamine

Step 1: Preparation of 1(S)-2-(5-chloro-2-thienyl)-1-hydroxy-1-methylethane

A solution of 2-chlorothiophene (8.17 g) in tetrahydrofuran (80 ml) is cooled to −30° C. and 1.6M n-butyllithium in hexanes (43.0 ml) is added dropwise. The mixture is stirred at −30° C. for about 1 hour, (S)-propylene oxide (4.00 g) is added, and the mixture is warmed to 0° C. and stirred at that temperature for about 3 hours. The reaction is quenched with saturated aqueous ammonium chloride solution, diluted with ether, and the layers separated. The organic layer is washed with brine, dried over magnesium sulfate, and concentrated in vacuo to give the desired product.

Step 2: Preparation of 1(R)-2-(5-chloro-2-thienyl)-1-methyl-1-phthalimidoethane

To a solution of 1(S)-2-(5-chloro-2-thienyl)-1-hydroxy-1-methylethane (8.8 g), triphenylphosphine (13.1 g), and phthalimide (7.35 g) in tetrahydrofuran (80 ml) is dropwise added diethyl azodicarboxylate (7.9 ml). The solution is stirred for about 18 hours and the solvent removed in vacuo. The residue is purified by flash chromatography, eluting with 20% hexanes in methylene chloride, to give the desired product.

Step 3: Preparation of 1(R)-2-(5-chloro-2-thienyl)-1-methylethylamine

1(R)-2-(5-chloro-2-thienyl)-1-methyl-1-phthalimidoethane (13.0 g) is dissolved in ethanol (75 ml) and hydrazine hydrate (2.5 ml) is added and the mixture stirred at reflux for about 1 hour. The mixture is cooled to room temperature, the solid removed by filtration, and the filtrate concentrated in vacuo. The residue is dissolved in ethyl acetate and this solution stirred with 5N aqueous hydrochloric acid. The layers are separated and the aqueous adjusted to ph>10 with 10% sodium hydroxide solution, then extracted with ethyl acetate. The organic solution is washed with brine, dried over magnesium sulfate, filtered, and concentrated in vacuo to give the desired product, $[\alpha]_D = -22.96°$ (c=11.5, methanol).

EXAMPLE 51

Preparation of 1(R)-2-(2-thienyl)-1-methylethylamine

Step 1: Preparation of 1(S)-2-(2-thienyl)-1-hydroxy-1-methylethane

Using essentially the procedure of Example 50, Step 1, the desired product is prepared from thiophene.

Step 2: Preparation of 1(R)-2-(2-thienyl)-1-methyl-1-phthalimidoethane

Using essentially the procedure of Example 50, Step 2, the desired product is prepared from 1(S)-2-(2-thienyl)-1-hydroxy-1-methylethane.

Step 3: Preparation of 1(R)-2-(2-thienyl)-1-methylethylamine

Using essentially the procedure of Example 50, Step 3, the desired product $[\alpha]_D = -15.6°$ (c=1, methanol) is prepared from 1(R)-2-(2-thienyl)-1-methyl-1-phthalimidoethane.

EXAMPLE 52

Preparation of
1(S)-2-(5-chloro-2-thienyl)-1-methylethylamine

Step 1: Preparation of 1(S)-2-(5-chloro-2-thienyl)-1-hydroxy-1-methylethane

To a stirred solution of 1(S)-2-(5-chloro-2-thienyl)-1-hydroxy-1-methylethane (5.70 g) in tetrahydrofuran (100 ml) is added triphenylphosphine (5.34 g) and benzoic acid (2.49 g). Diethyl azodicarboxylate (3.22 ml) is added dropwise and the mixture stirred at room temperature for about 18 hours. The solvent is removed in vacuo. The residue is purified by flash chromatography, eluting with 30% hexanes in methylene chloride, to give (R)-3-(5-chloro-2-thienyl)-2-propyl benzoate. The ester (3.91 g) is dissolved in dioxane (50 ml) and 20% aqueous sodium hydroxide (15 ml) is added. The mixture is heated at 55° C. for 3 hours and concentrated in vacuo. The residue is taken up in ethyl acetate (200 ml) and the organic layer washed with brine, dried over magnesium sulfate, filtered, concentrated in vacuo to give the desired product.

Step 2: Preparation of 1(S)-2-(5-chloro-2-thienyl)-1-methylethylamine

Using essentially the procedure of Example 50, Steps 2 and 3, the desired product, $\alpha_D = +21.71°$ (c=1.1, methanol) is prepared from 1(S)-2-(5-chloro-2-thienyl)-1-methylethane.

Using essentially the procedures of Examples 50, 51, and 52, the following compounds are prepared from appropriate starting materials.

EXAMPLE 53
1(R)-2-(benzothiophen-2-yl)-1-methylethylamine

EXAMPLE 54
1(S)-2-(2-thienyl)-1-methylethylamine, $\alpha_D = 15.5°$ (c=1, methanol)

EXAMPLE 55
1(R)-2-(3-bromo-2-thienyl)-1-methylethylamine

EXAMPLE 56
1(R)-2-[5-(2-pyridyl)-2-thienyl]-1-methylethylamine

EXAMPLE 57
1(R)-2-[5-(2-thienyl)-2-thienyl]-1-methylethylamine

EXAMPLE 58
1(R)-2-(5-phenyl-2-thienyl)-1-methylethylamine

EXAMPLE 59
1(R)-2-(5-methoxy-2-thienyl)-1-methylethylamine

EXAMPLE 60
1(R)-2-(5-methyl-2-thienyl)-1-methylethylamine

EXAMPLE 61
1(R)-2-(5-bromo-2-thienyl)-1-methylethylamine

EXAMPLE 62
1(R)-2-(5-iodo-2-thienyl)-1-methylethylamine

EXAMPLE 63
1(R)-2-(5-methylthio-2-thienyl)-1-methylethylamine

EXAMPLE 64
1(R)-2-(5-methylsulfonyl-2-thienyl)-1-methylethylamine

EXAMPLE 65
1(R)-2-(5-ethyl-2-thienyl)-1-methylethylamine

EXAMPLE 66
1(R)-2-(5-n-heptyl-2-thienyl)-1-methylethylamine

EXAMPLE 67
1(R)-2-(3-methyl-2-thienyl)-1-methylethylamine

EXAMPLE 68
1(R)-2-(4-methyl-2-thienyl)-1-methylethylamine

EXAMPLE 69
1(R)-2-(3-chloro-2-thienyl)-1-methylethylamine, $[\alpha]_D = -6.1°$ (c=1, methanol)

EXAMPLE 70
1(R)-2-(4-chloro-2-thienyl)-1-methylethylamine

EXAMPLE 71
1(R)-2-(3-chloro-5-phenyl-2-thienyl)-1-methylethylamine

EXAMPLE 72
1(R)-2-(5-bromo-2-chloro-2-thienyl)-1-methylethylamine

EXAMPLE 73
1(R)-2-(4-methyl-5-chloro-2-thienyl)-1-methylethylamine

EXAMPLE 74
1(R)-2-(2,5-dichloro-3-thienyl)-1-methylethylamine

Compounds of the present invention are useful as anti-hypertensive agents for the treatment of high blood pressure; they also increase coronary blood flow, and, accordingly, are useful in the treatment of myocardial ischemia.

Compounds within the scope of this invention exhibit activity in standard $A_1/A_2$ receptor binding assays for the determination of adenosine receptor agonist activity in mammals. Exemplary test procedures which are useful in determining the receptor binding affinity of compounds of the present invention are described below.

A. IN VITRO ADENOSINE RECEPTOR BINDING AFFINITY DETERMINATION $A_1$ Receptor Binding Affinity was determined by competition assay based on ligand displacement of $^3$H-CHA (cyclohexyl adenosine) [Research Biochemicals Inc., Natick, Mass.] from receptor using a membrane preparation of whole rat brain, according to the procedure of R. F. Bruns et al., Mol. Pharmacol., 29: 331 (1986). Non-specific binding was assessed in the presence of 1 mM theophylline.

$A_2$ receptor binding affinity was determined by a similar assay technique, based on ligand displacement of $^3$H-CGS 21680, a known $A_2$ receptor-specific adenosine agonist, from receptor, using membranes from rat brain striatum. Non-specific binding was assessed in the presence of 20 μm 2-chloroadenosine.

The assays were run in glass test tubes in duplicate at 25° C. Once the membranes were added, the tubes were vortexed and incubated at 25° C. for 60 minutes ($A_1$ assay) or 90 minutes ($A_2$ assay) on a rotary shaker. The assay tubes were vortexed halfway through the incubation and again near the end. The assays were terminated by rapid filtration through 2.4 cm GF/B filters using a Brandel Cell Harvestor. The test tubes were washed three times with cold 50 mM tris-HCl (pH 7.7 or 7.4), with filtration being completed within 15 seconds. The damp filter circles were placed in glass scintillation vials filled with 10 ml of Aquasol II (New England Nuclear). The vials were allowed to shake overnight on a rotary shaker and were placed into a liquid scintillation analyzer for two minute counts. $IC_{50}$ values for receptor binding, i.e. the concentration at which a compound of the invention displaced the radiolabeled standard, were obtained using a curve-fitting computer program (RS/1, Bolt, Beranek and Newman, Boston, Mass.).

B. IN VITRO VASORELAXATION DETERMINATION IN ISOLATED SWINE CORONARY ARTERIES

Swine coronary arteries were obtained from a local slaughter house, dissected carefully and cleaned of fat, blood and adhering tissue. Rings approximately 2–3 mm wide were cut and transferred to water-jacketed tissue baths (10 ml) filled with warm (37° C.), oxygenated ($O_2/CO_2$:95%/5%) Krebs-Henseleit buffer and mounted on L-shaped hooks between stainless steel rods and a force transducer. The composition of the Krebs buffer is as follows (mM): NaCl, 118; KCl, 4.7; CaCl2, 2.5; MgSO4, 1.2; KH2PO4, 1.2; NaHCO3, 25.0; and glucose, 10.0. Rings were equilibrated for 90 minutes with frequent buffer changes at a resting tension of 5 g. In order to assure optimal tension development, arterial rings were primed twice with 36 mM KCl and once with 10 μm. PGF2α, before being exposed to 3 μM PGF2α. When isometric tension had reached a steady state, accumulative doses of the adenosine agonists of the invention (usually 1 mM to 100 μM, in half logs) were added to the baths. Tension achieved with 3 μM PGF2α was considered equivalent to 100%; all other values were expressed as a percentage of that maximum. $IC_{50}$ values for relaxation, i.e. the concentration at which a compound of the invention caused a 50% reduction in tension, were determined using the above-mentioned linear curve fitting computer program.

C. IN VIVO MEAN ARTERIAL BLOOD PRESSURE (MAP) AND HEART RATE (HR) DETER-

MINATIONS IN NORMOTENSIVE ANESTHETIZED AND SPONTANEOUSLY HYPERTENSIVE RAT

1. Anesthetized Rat

Normotensive rats were anesthetized with sodium pentobarbital (50 mg/kg, i.p.) and placed on a heated surgical table. Cannulas were inserted into the femoral artery and veined to allow the measurement of arterial pressure and to facilitate the intravenous administration of test compounds. The animals was allowed to equilibrate for 10 minutes after surgery. Mean arterial pressure was continuously measured and recorded and heart rate was monitored using the arterial pressure pulse to trigger a cardiotachometer. After baseline parameters were established and recorded, increasing doses (1, 3, 10, 30, 100, 300 and 1000 µg/kg) of the compound of the invention to be tested were administered intravenously. Maximal changes in the cardiovascular parameters were observed after each dose of the adenosine agonist. Only one compound was administered per rat. The potency of the compounds to lower heart rate and mean arterial pressure were assessed by determining the dose of the agent necessary to lower the heart rate or arterial pressure by 25% ($ED_{25}$).

2. Spontaneously Hypertensive Rat (SHR)

The oral antihypertensive activity of compounds of the invention were examined in conscious spontaneously hypertensive rats. The rats were anesthetized with sodium pentabarbatol (50 mg/kg i.p.). A telemetry transducer was implanted into the rats abdomen via midline incision. The cannula of the transducer was inserted into the abdomenal aorta to allow direct measurement of arterial pressure in the conscious SHR. The transducer was secured to the abdomenal wall. After recovery from surgery (minimum of seven days), the SHR were placed on a receiver plate and the transducer/transmitter was activated. Systolic, diastolic and mean arterial pressure and heart rate were recorded for 1.5 hours in the unrestrained conscious rat to establish a stable baseline. Each rat then received a single dose of the compound of the invention to be tested, or vehicle, and changes in arterial pressure and heart rate were monitored for 20 hours and recorded.

Table II presents results of the biological activity determinations for exemplary compounds, and for the compound of Example 6, Step 1, within the scope of the invention.

TABLE II

| Ex. No. | Adenosine Receptor Binding Activity/ $IC_{50}$ (nM) | | Vasorelaxation in Swine Coronary Artery/ $IC_{50}$ (µM) | Blood Press/Heart Rate | | | | |
|---|---|---|---|---|---|---|---|---|
| | | | | Anesthetized Rat | | | SHR* | |
| | $A_1$ | $A_2$ | | MAP/$ED_{25}$ (µg/kg) | HR/$ED_{25}$ (µg/kg) | Dose (mg/kg) | MAP/% | HR/% |
| 4 | 1.66 | 55 | 0.73 | 13 | 19 | 5 | 28 (D) | 20 (D) |
| 5 | 4.26 | 91 | 0.068 | — | — | — | — | — |
| 6 | 2.69 | 12.88 | 0.021 | — | — | 1 | 18 (D) | 7 (I) |
| 6(1) | >1000 | >1000 | 19.1 | — | — | — | — | — |
| 7 | 3.5 | 28 | 4 | 6 | 18 | 5 | 45 (D) | 22 (D) |
| 8 | 5 | 138 | — | 10 | 23 | — | — | — |
| 9 | 4 | 1000 | 11.9 | 5 | 4 | — | — | — |
| 10 | 3.8 | >1000 | — | — | — | — | — | — |
| 11 | 7.4 | >1000 | — | — | — | — | — | — |
| 12 | 23 | 224 | 0.5 | 4 | 17 | — | — | — |
| 13 | 41 | 191 | 0.24 | 3 | >10 | — | — | — |
| 14 | 79.4 | >1000 | — | — | — | — | — | — |
| 15 | 4.07 | 1000 | 2.45 | 1.5 | 1.4 | — | — | — |
| 16 | 1.7 | >1000 | — | — | — | — | — | — |
| 17 | 67.6 | 5248 | 18.77 | — | — | — | — | — |
| 18 | 166 | 52 | 0.46 | 2 | >10 | — | — | — |
| 19 | 36 | 1000 | 0.75 | — | — | — | — | — |
| 20 | 3.98 | 158 | — | — | — | — | — | — |
| 21 | 0.09 | 14.8 | — | — | — | — | — | — |
| 22 | 2.69 | 29.5 | 0.1 | — | — | — | — | — |
| 23 | 0.32 | 891 | 4.4 | 6 | 7 | — | — | — |
| 24 | >1000 | >1000 | — | 6 | >10 | 5 | 17 (D) | 6 (I) |
| 25 | 1258.3 | 355 | 0.64 | — | — | — | — | — |
| 26 | 87.1 | 63.1 | 0.082 | 4 | >30 | 2.5 | 41 (D) | 3 (I) |
| 27 | 5.01 | 29.5 | 0.043 | — | — | 1 | 27 (D) | 1 (I) |
| 28 | 417 | >1000 | — | — | — | — | — | — |
| 29 | 35.48 | >1000 | 22 | 16 | 31 | 5 | 18 (D) | 12 (D) |
| 30 | 562 | >1000 | 12.1 | 6 | >10 | — | — | — |
| 31 | 0.03 | 8.9 | — | — | — | — | — | — |
| 32 | 0.049 | 45 | — | — | — | — | — | — |
| 34 | 1.6 | 23 | 0.072 | — | — | — | — | — |
| 35 | 1087 | 6351 | 3.3 | — | — | — | — | — |
| 36 | 8.8 | 43.4 | 0.493 | — | — | — | — | — |
| 37 | 16.2 | 110 | 0.45 | — | — | — | — | — |
| 38 | 5.7 | 55.5 | 0.47 | — | — | — | — | — |
| 39 | 3.98 | 46.8 | — | — | — | — | — | — |
| 40 | 9.3 | 68.8 | .283 | — | — | — | — | — |
| 41 | 14.2 | 158 | — | — | — | — | — | — |
| 42 | >1000 | >10000 | 2.44 | — | — | — | — | — |
| 43 | 8428 | >10000 | 7.83 | — | — | — | — | — |
| 44 | 55 | 331 | 0.316 | — | — | — | — | — |
| 45 | 6351 | >10000 | 4.1 | — | — | — | — | — |
| 46 | 13.5 | 81 | 3.52 | — | — | — | — | — |
| 47 | 23 | 2818 | 5.7 | — | — | — | — | — |
| 48 | 8.35 | 1445 | — | — | — | — | — | — |

TABLE II-continued

| Ex. No. | Adenosine Receptor Binding Activity/ IC50 (nM) | | Vasorelaxation in Swine Coronary Artery/ IC50 (μM) | Blood Press/Heart Rate | | | | |
|---|---|---|---|---|---|---|---|---|
| | | | | Anesthetized Rat | | | SHR* | |
| | $A_1$ | $A_2$ | | MAP/ED25 (μg/kg) | HR/ED25 (μg/kg) | Dose (mg/kg) | MAP/% | HR/% |
| 49 | 69 | 2884 | 9.81 | — | — | — | — | — |

*D signifies decrease; I signifies increase

The compounds of this invention can be normally administered orally or parenterally, in the treatment of patients suffering from hypertension or myocardial ischemia. As used herein, the term "patients" includes humans and other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of the adenosine agonists to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carder can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for administration by intramuscular and subcutaneous injection. The aqueous solutions, including those of the salts dissolved in pure distilled water, are suitable for administration by intravenous injection, provided that their pH is properly adjusted, and that they are suitably buffered, made isotonic with sufficient saline or glucose and sterilized by heating or by microfiltration.

The dosage regimen used in carrying out the methods of this invention is that which insures maximum therapeutic response until improvement is obtained and thereafter the minimum effective level which gives relief. Thus, in general, the dosages are those that are therapeutically effective in lowering blood pressure in the treatment of hypertension, or in increasing coronary blood flow in the treatment of myocardial ischemia. In general, the oral dose may be between about 0.1 and about 100 (preferably in the range of 1 to 10 mg/kg), and the i.v. dose about 0.01 to about 10 mg/kg (preferably in the range of 0.1 to 5 mg/kg), bearing in mind, of course, that in selecting the appropriate dosage in any specific case, consideration must be given to the patient's weight, general health, age and other factors which may influence response to the drug.

The compounds of the invention may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally about 1 to about 4 times per day. It is anticipated that many patients will require no more than about one to about two doses daily.

It is also anticipated that the present invention would be useful as an injectable dosage form which may be administered in an emergency to a patient suffering from acute hypertension or myocardial ischemia. Such treatment may be followed by intravenous infusion of the active compound and the amount of compound infused into such a patient should be effective to achieve and maintain the desired therapeutic response.

What is claimed is:

1. A compound of the formula

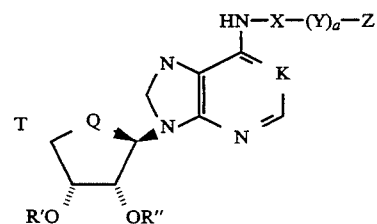

wherein:
K is CH;
Q is $CH_2$;
T is

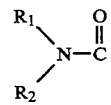

or $R_3O$—$CH_2$;
X is a straight or branched chain alkylene, cycloalkylene or cycloalkenylene group;

Y is NR₄, O or S;
a=0 or 1;
Z is of the formula

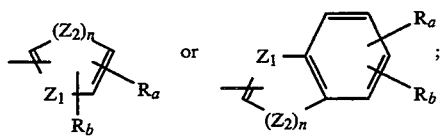

Z₁ is N, CR₅, (CH)$_m$—CR₅ or (CH)$_m$—N, m being 1 or 2;
Z₂ is N, NR₆, O or S, n being 0 or 1;
R₁, R₂, R₃, R₄, R₅ and R₆ are independently H, alkyl, aryl or heterocyclyl;
R$_a$ and R$_b$ are independently H, OH, alkyl, hydroxyalkyl, alkyl mercaptyl, thioalkyl, alkoxy, alkyoxyalkyl, amino, alkyl amino, carboxyl, acyl, halogen, carbamoyl, alkyl carbamoyl, aryl or heterocyclyl; and
R' and R" are independently hydrogen, alkyl, aralkyl, carbamoyl, alkyl carbamoyl, dialkylcarbamoyl, acyl, alkoxycarbonyl, aralkoxycarbonyl, aryloxycarbonyl, or R' and R" together may form

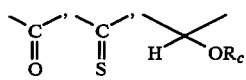

where r$_c$ is hydrogen or alkyl,

where R$_d$ and R$_e$ are independently hydrogen, alkyl, or together with the carbon atom to which they are attached may form a 1,1-cycloalkyl group;
provided that when X is straight chain alkylene and Q is oxygen, then Z represents a heterocyclyl including at least two heteroatoms;
or a pharmaceutically acceptable salt thereof.

2. A compound of claim 1 wherein R' and R" are H.

3. A compound according to claim 2, wherein X is a lower alkylene which can be branched and substituted by at least one CH₃, CH₃CH₂, Cl, F, CF₃ or CH₃O.

4. A compound according to claim 2, wherein Z is

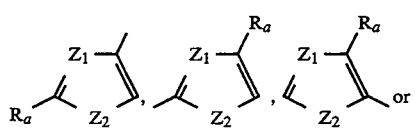

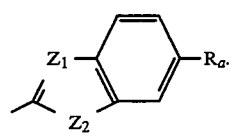

5. A compound of the formula

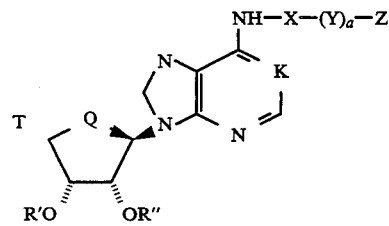

wherein:
K is CH;
Q is CH₂ or O;
T is

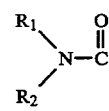

or R₃O—CH₂;
X is a straight or branched chain alkylene, cycloalkylene or cycloalkenylene group;
Y is NR₄, O or S;
a=0 or 1;
Z is a substituted or unsubstituted thiazolyl group or a substituted or unsubstituted benzothiazolyl group;
R₁, R₂, R₃, and R₄ are independently H, alkyl, aryl or heterocyclyl; and
R' and R" are independently hydrogen, alkyl, aralkyl, carbamoyl, alkylcarbamoyl, dialkylcarbamoyl, acyl, alkoxycarbonyl, aralkoxycarbonyl, aryloxycarbonyl, or R' and R" together may form

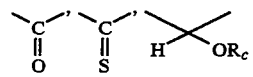

where R$_c$ is hydrogen or alkyl,

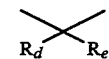

where R$_d$ and R$^e$ are independently hydrogen, alkyl, or together with the carbon atom to which they are attached may form a 1,1-cycloalkyl group;
or a pharmaceutically acceptable salt thereof.

6. A compound as claimed in claim 4, wherein X represents the alkylene moiety CR₉H—CH₂, wherein R₉ hydrogen, lower alkyl, halo, halo lower alkyl or lower alkoxy.

7. A compound as claimed in claim 6, wherein the alkylene carbon to which R₉ is bonded is a chiral center.

8. A compound according to claim 7, wherein R₉ is methyl or ethyl.

9. A compound according to claim 7, wherein said chiral center is substantially exclusively R.

10. A compound according to claim 1 wherein: K is CH; Q is CH₂; and T is R₁R₂N—C=O.

11. A compound according to claim 2 which is [1-S-[1α,2β,3β,4α(S*)]]-4-[7-[[2-(5-chloro-2-thienyl)-1-methylethyl]amino]-3H-imidazo[4,5-b]pyridin-3-yl]-N-ethyl-2,3-dihydroxycyclopentane-carboxamide, [1S--[1α,2β,3β,4α]]-4-[7-[[2-(3-chloro-2-thienyl)-1-ethylethyl]amino]-3H-imidazo[4,5-b]pyridin-3-yl]-N-ethyl-2,3-dihydroxycyclopentane-carboxamide, [1S-1α,2β,3β,4α]]-4-[7-[[2-(2-thienyl)-1-isopropylethyl-]amino]-3H-imidazo[4,5-b]pyridin-3-yl]-N-ethyl-2,3-dihydroxycyclopentanecarboxamide, [1S-[1α,2β,3β,-4α(S*)]]-4-[[2-(3-chloro-2-thienyl)-1-ethylethyl]amino]-3H-imidazo[4,5-b]pyridin-3yl]-N-ethyl-2,3-dihydroxycyclopentane-carboxamide, [1S-[1α,2β,3β,4α(S*)]]-4-[7-[[2-(2-thienyl)-1-methylethyl]amino]-3H-imidazo[4,5b]pyridin-3-yl]-N-ethyl-2,3-dihydroxycyclopentane-carboxamide, or [1S-[1α,2β,3β,4α]]-4-[7-[[2-(5-chloro-2-thienyl)-1-ethylethyl]amino]-3H-imidazo[4,5b]pyridin-3-yl]-N-ethyl-2,3-dihydroxycyclopentane-carboxamide, or a pharmaceutically acceptable salt thereof.

12. A composition for treating a cardiovascular disease marked by hypertension of myocardial ischemia, said composition comprising an antihypertensive effective amount, or an anti-ischemic effective amount of a compound according to claim 1 and a pharmaceutically acceptable carrier thereof.

13. A method for treating a patient suffering from hypertension, comprising administering to said patient an effective blood pressure lowering amount of a compound according to claim 1.

14. A method for treating a patient suffering from myocardial ischemia, comprising administering to said patient an effective antiischemic amount of a compound according to claim 1.

15. A compound according to claim 11 which is [1S-[1α,2β,3β,4α(S*)]]-4-[7-[[2-(3-chloro-2-thienyl)-1-ethylethyl]amino]-3H -imidazo[4,5-b]pyridin-3-yl]-N-ethyl-2,3-dihydroxycyclopentanecarboxamide, or a pharmaceutically acceptable salt thereof.

16. A composition according to claim 12 comprising [1S[1α,2β,3β,4α(S*)]]-4-[7-[[2-(3-chloro-2-thienyl)-1-ethylethyl]amino]-3H-imidazo[4,5-b]pyridin-3-yl]-N-ethyl-2,3-dihydroxycyclopentanecarboxamide, or a pharmaceutically acceptable salt thereof.

17. A method according to claim 13, wherein the compound administered is [1S-[1α,2β,3β,4'(S*)]]-4-[7-[[2-(3chloro-2-thienyl)-1-ethylethyl]amino]-3H-imidazo[4,5-b]pyridin-3yl]-N-ethyl-2,3-dihydroxycyclopentanecarboxamide, or a pharmaceutically acceptable salt thereof.

18. A method according to claim 14, wherein the compound administered is [1S-[1α,2β,3β,4α(S*)]]-4-[7-[[2-(3-chloro-2-thienyl-1-ethylethyl]amino]-3H-imidazo[4,5-b]pyridin-3-yl]-N-ethyl-2,3-dihydroxycyclopentanecarboxamide, or a pharmaceutically acceptable salt thereof.

* * * * *

UNITED STATES PATENT AND TRADEMARK OFFICE
CERTIFICATE OF CORRECTION

PATENT NO. : 5,364,862
DATED : November 15, 1994
INVENTOR(S) : Alfred P. Spada et al.

It is certified that error appears in the above-indentified patent and that said Letters Patent is hereby corrected as shown below:

On Page 2, under OTHER PUBLICATIONS, in the publication by Prasad, et al., delete "Modifications for the 5' Position of Purine Nucleosides. 2. Synthesis and Some Cardiovascular Properties of" and insert --Modifications of the 5' Position of Purine Nucleosides. 2. Synthesis and Some Cardiovascular Properties of Adenosine-5'-(N-substituted)carboxamides--.

On Page 2, under OTHER PUBLICATIONS, in the publication by Houston, et al., delete "Potential Inhibitors of S-Adenosylmethionine-Dependent Methyltransferasess, 9,2',3'-Diaaldehyde Derivatives" and insert --Potential Inhibitors of S-Adenosylmethionine-Dependent Methyltransferases. 9. 2',3'-Dialdehyde Derivatives of Carbocyclic Purine Nucleosides as Inhibitors of S-Adenosylhomocyteine Hydrolase--.

On page 2, under OTHER PUBLICATIONS, in the publication by Franchetti, et al., delete "Ribofuraanosylvaamino" and insert --Ribofuranosylamino--.

UNITED STATES PATENT AND TRADEMARK OFFICE
CERTIFICATE OF CORRECTION

PATENT NO. : 5,364,862
DATED : November 15, 1994
INVENTOR(S) : Alfred P. Spada et al.

It is certified that error appears in the above-indentified patent and that said Letters Patent is hereby corrected as shown below:

On page 2, under OTHER PUBLICATIONS, in the publication by Prasad, et al., delete "Modification of the 5' position of Purine Nucleosides. 1. Synthesis and Biological Properties of Alkyl" and insert --Modification of the 5' position of Purine Nucleosides. 1. Synthesis and Biological Properties of Alkyl Adensosine-5'-carboxylates--.

On page 2, under OTHER PUBLICATIONS, in the publication by Cristalli, et al., delete "Adenosine and 2-Chloradenosine Deaza#Analoges as Adenosine receptor aagonists" and insert --Adenosine and 2-Chloroadenosine Deaza-Analogues as Adenosine Receptor Agonists--.

At column 4, line 33, delete "ration" and insert --ratio--.

UNITED STATES PATENT AND TRADEMARK OFFICE
CERTIFICATE OF CORRECTION

PATENT NO. : 5,364,862

DATED : November 15, 1994

INVENTOR(S) : Alfred P. Spada et al

It is certified that error appears in the above-indentified patent and that said Letters Patent is hereby corrected as shown below:

At column 5, line 59, delete

"  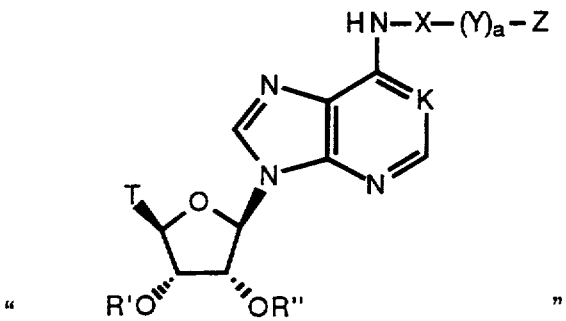  "

and insert

--  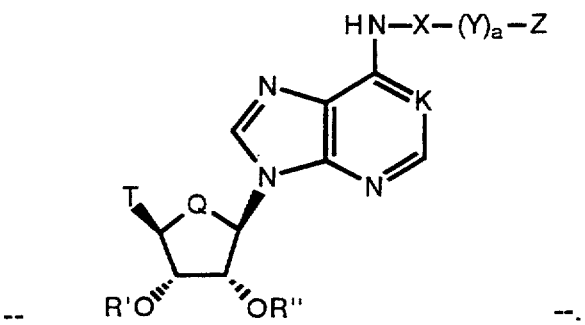  --.

At column 6, line 3, delete "is $R_2$".

UNITED STATES PATENT AND TRADEMARK OFFICE
CERTIFICATE OF CORRECTION

PATENT NO. : 5,364,862  Page 4 of 6
DATED : November 15, 1994
INVENTOR(S) : Alfred P. Spada et al It is certified that error appears in the above-indentified patent and that said Letters Patent is hereby corrected as shown below:

At column 11, line 33, delete " 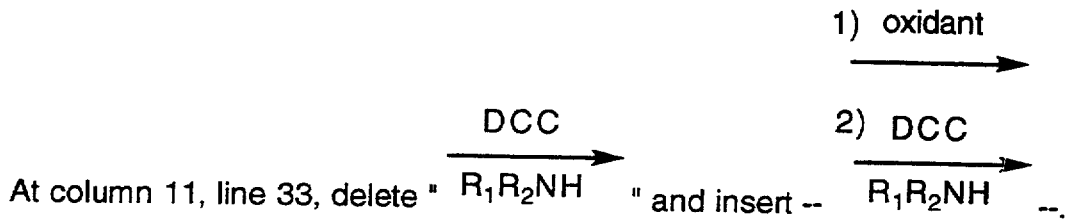 " and insert --

At column 17, lines 6-24, delete

" 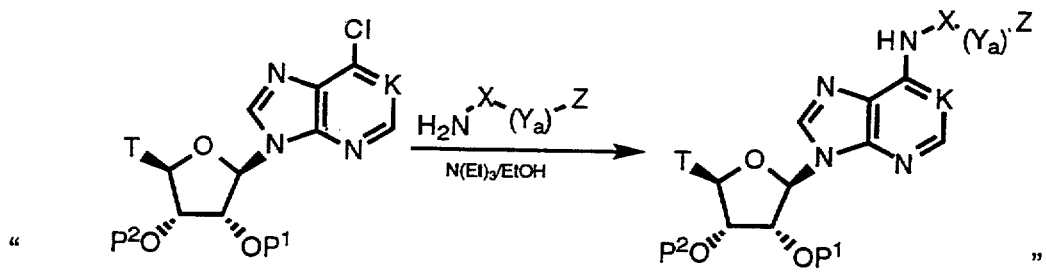 "

and insert

UNITED STATES PATENT AND TRADEMARK OFFICE
CERTIFICATE OF CORRECTION

PATENT NO. : 5,364,862
DATED : November 15, 1994
INVENTOR(S) : Alfred P. Spada et al.

It is certified that error appears in the above-indentified patent and that said Letters Patent is hereby corrected as shown below:

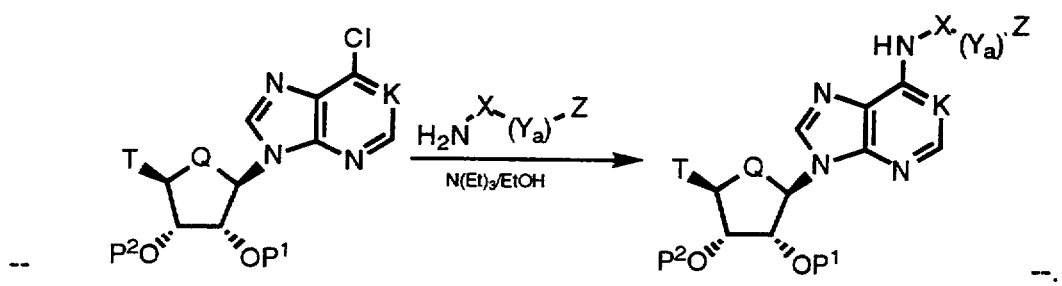

At column 42, line 50, and at column 44, line 5, delete

UNITED STATES PATENT AND TRADEMARK OFFICE
CERTIFICATE OF CORRECTION

PATENT NO. : 5,364,862

DATED : November 15, 1994

INVENTOR(S) : Alfred P. Spada et al

It is certified that error appears in the above-indentified patent and that said Letters Patent is hereby corrected as shown below:

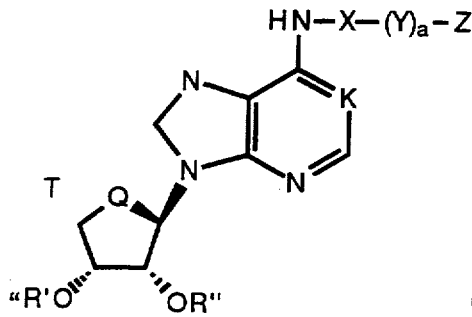 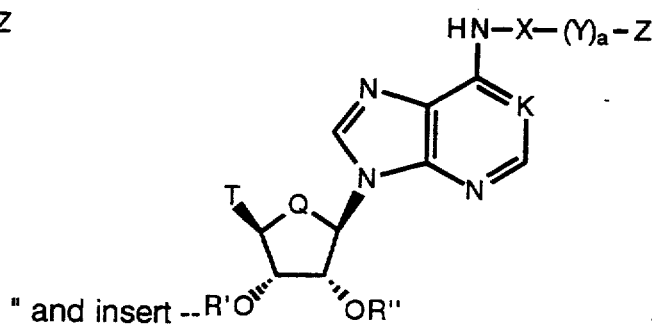

At column 43, line 35, delete "$r_c$" and insert --$R_c$--.

Signed and Sealed this

Tenth Day of September, 1996

Attest:

BRUCE LEHMAN

Attesting Officer     Commissioner of Patents and Trademarks